(12) United States Patent
Bonadio et al.

(10) Patent No.: US 8,157,817 B2
(45) Date of Patent: Apr. 17, 2012

(54) SURGICAL INSTRUMENT

(75) Inventors: Frank Bonadio, Bray (IE); Alan Reid, Clontart (IE); Derek Young, Blackrock (IE); John Butler, Blackrock (IE); Frank Harewood, Kingston (IE)

(73) Assignee: Atropos Limited, Wicklow (IE)

( * ) Notice: Subject to any disclaimer, the term of this patent is extended or adjusted under 35 U.S.C. 154(b) by 434 days.

(21) Appl. No.: 10/347,313

(22) Filed: Jan. 21, 2003

(65) Prior Publication Data
US 2003/0236549 A1 Dec. 25, 2003

Related U.S. Application Data

(63) Continuation of application No. PCT/IE01/00094, filed on Jul. 23, 2001.

(30) Foreign Application Priority Data

| Jul. 21, 2000 | (IE) | 2000/0591 |
| Dec. 21, 2000 | (IE) | 2000/1061 |
| Dec. 21, 2000 | (IE) | 2000/1072 |

(51) Int. Cl.
*A61B 17/28* (2006.01)

(52) U.S. Cl. ........................ 606/148; 606/170

(58) Field of Classification Search .................. 606/148, 606/170, 171, 174, 180, 205–211
See application file for complete search history.

(56) References Cited

U.S. PATENT DOCUMENTS

| 1,620,828 A | 3/1927 | Molony |
| 1,708,578 A | 4/1929 | Hyde |
| 2,047,535 A | 7/1936 | Wappler |
| 2,555,017 A | 5/1951 | Tuthill |
| 2,888,928 A | 6/1959 | Seiger |
| 2,907,321 A | 10/1959 | Rubens |
| 3,144,020 A | 8/1964 | Zingale |
| 3,452,615 A | 7/1969 | Gregory, Jr. |
| 3,605,725 A | 9/1971 | Bentov |
| 3,831,587 A | 8/1974 | Boyd |
| 3,960,143 A | 6/1976 | Terada |
| 4,033,618 A | 7/1977 | Lamb |
| 4,108,211 A | 8/1978 | Tanaka |
| 4,327,711 A | 5/1982 | Takagi |
| 4,483,562 A | 11/1984 | Schoolman |
| 4,610,383 A | 9/1986 | Rothfuss et al. |

(Continued)

FOREIGN PATENT DOCUMENTS
EP 0791330 6/2005
(Continued)

*Primary Examiner* — Kevin T Truong
(74) *Attorney, Agent, or Firm* — Finnegan, Henderson, Farabow, Garrett & Dunner, L.L.P.

(57) ABSTRACT

A minimally invasive surgical instrument having an elongate stem extending between a proximal end which in use is located externally of an operating space and a distal end which in use is located within an operating space. At least a portion of the stem is malleable to facilitate manipulation of the stem in the operating space and then to maintain the stem in the manipulated position and/or orientation within the operating space. The instrument has an end effector at the distal end of the stem, the end effector having a proximal main body and distal operating means, such as graspers or cutters. The instrument has at least one joint for independent movement of the end effector main body in at least one direction relative to the distal end of the stem for enhanced degrees of freedom of the instrument.

20 Claims, 40 Drawing Sheets

U.S. PATENT DOCUMENTS

| | | | |
|---|---|---|---|
| 4,641,652 A | 2/1987 | Hutterer et al. |
| 4,646,745 A | 3/1987 | Noiles |
| 4,686,965 A | 8/1987 | Bonnet et al. |
| 4,708,434 A | 11/1987 | Tsuno |
| 4,714,075 A | 12/1987 | Krauter et al. |
| 4,754,909 A | 7/1988 | Barker et al. |
| 4,759,348 A | 7/1988 | Cawood |
| 4,945,920 A | 8/1990 | Clossick |
| 4,950,273 A | 8/1990 | Briggs |
| 5,025,804 A | 6/1991 | Kondo |
| 5,035,695 A | 7/1991 | Weber, Jr. et al. |
| 5,143,475 A | 9/1992 | Chikama |
| 5,147,356 A | 9/1992 | Bhatta |
| 5,152,744 A | 10/1992 | Krause et al. |
| 5,171,256 A | 12/1992 | Smith et al. |
| 5,242,409 A | 9/1993 | Buelna |
| 5,250,046 A | 10/1993 | Lee |
| 5,279,567 A | 1/1994 | Ciaglia et al. |
| 5,282,806 A | 2/1994 | Haber et al. |
| 5,304,183 A | 4/1994 | Gourlay et al. |
| 5,320,611 A | 6/1994 | Bonutti et al. |
| 5,354,311 A | 10/1994 | Kambin et al. |
| 5,383,861 A | 1/1995 | Hempel et al. |
| 5,396,879 A | 3/1995 | Wilk et al. |
| 5,423,848 A | 6/1995 | Washizuka et al. |
| 5,431,676 A | 7/1995 | Dubrul et al. |
| 5,454,827 A | 10/1995 | Aust et al. |
| 5,456,684 A | 10/1995 | Schmidt et al. |
| 5,458,608 A | 10/1995 | Wortrich |
| 5,527,326 A | 6/1996 | Hermann et al. |
| 5,540,706 A | 7/1996 | Aust et al. |
| 5,618,294 A | 4/1997 | Aust et al. |
| 5,626,607 A | 5/1997 | Malecki et al. |
| 5,643,294 A * | 7/1997 | Tovey et al. ............... 606/170 |
| 5,669,926 A | 9/1997 | Aust et al. |
| 5,720,759 A | 2/1998 | Green et al. |
| 5,741,286 A | 4/1998 | Recuset |
| 5,779,727 A | 7/1998 | Orejola |
| 5,840,077 A | 11/1998 | Rowden et al. |
| 5,851,212 A | 12/1998 | Zirps et al. |
| 5,885,238 A | 3/1999 | Stevens et al. |
| 5,891,147 A | 4/1999 | Moskovitz et al. |
| 5,894,843 A | 4/1999 | Benetti et al. |
| 5,899,914 A | 5/1999 | Zirps et al. |
| 5,921,915 A | 7/1999 | Aznoian et al. |
| 5,921,918 A | 7/1999 | Riza |
| 5,925,064 A | 7/1999 | Meyers et al. |
| 5,938,678 A | 8/1999 | Zirps et al. |
| 5,967,997 A | 10/1999 | Turturro et al. |
| 6,001,096 A | 12/1999 | Bissinger et al. |
| 6,001,114 A | 12/1999 | Ouchi |
| 6,036,641 A | 3/2000 | Taylor et al. |
| 6,048,339 A | 4/2000 | Zirps et al. |
| 6,050,266 A | 4/2000 | Benetti et al. |
| 6,059,816 A | 5/2000 | Moenning |
| 6,077,286 A | 6/2000 | Cuschieri et al. |
| 6,077,287 A | 6/2000 | Taylor et al. |
| 6,077,290 A | 6/2000 | Marini |
| 6,126,633 A | 10/2000 | Kaji et al. |
| 6,129,713 A | 10/2000 | Mangosong et al. |
| 6,139,563 A | 10/2000 | Cosgrove, III et al. |
| 6,159,146 A | 12/2000 | El Gazayerli |
| 6,159,200 A | 12/2000 | Verdura et al. |
| 6,213,941 B1 | 4/2001 | Benetti et al. |
| 6,251,120 B1 | 6/2001 | Dorn |
| 6,290,644 B1 | 9/2001 | Green, II et al. |
| 6,454,783 B1 | 9/2002 | Piskun |
| RE38,018 E | 3/2003 | Anctil et al. |
| 6,647,281 B2 | 11/2003 | Morency |
| 6,821,285 B2 | 11/2004 | Laufer et al. |
| 7,083,636 B2 | 8/2006 | Kortenbach |
| 7,147,650 B2 | 12/2006 | Lee |
| 7,214,236 B2 | 5/2007 | Kieturakis et al. |
| 7,229,456 B2 | 6/2007 | Lang et al. |
| 7,270,658 B2 | 9/2007 | Woloszko et al. |
| 7,338,513 B2 | 3/2008 | Lee et al. |
| 7,364,582 B2 | 4/2008 | Lee |
| 2001/0025136 A1 | 9/2001 | Leonard et al. |
| 2002/0103498 A1 | 8/2002 | Pagedas |
| 2003/0028179 A1 | 2/2003 | Piskun |
| 2003/0045834 A1 | 3/2003 | Wing et al. |
| 2004/0138525 A1 | 7/2004 | Saddat et al. |
| 2005/0065543 A1 | 3/2005 | Kahle et al. |
| 2005/0085693 A1 | 4/2005 | Belson et al. |
| 2005/0096694 A1 | 5/2005 | Lee |
| 2006/0206101 A1 | 9/2006 | Lee |
| 2007/0049966 A1 | 3/2007 | Bonadio et al. |
| 2007/0244358 A1 | 10/2007 | Lee |
| 2007/0287993 A1 | 12/2007 | Hinman et al. |

FOREIGN PATENT DOCUMENTS

| | | |
|---|---|---|
| WO | WO 98/22030 | 5/1998 |
| WO | WO 99/15089 | 4/1999 |
| WO | WO 99/42036 | 8/1999 |

* cited by examiner

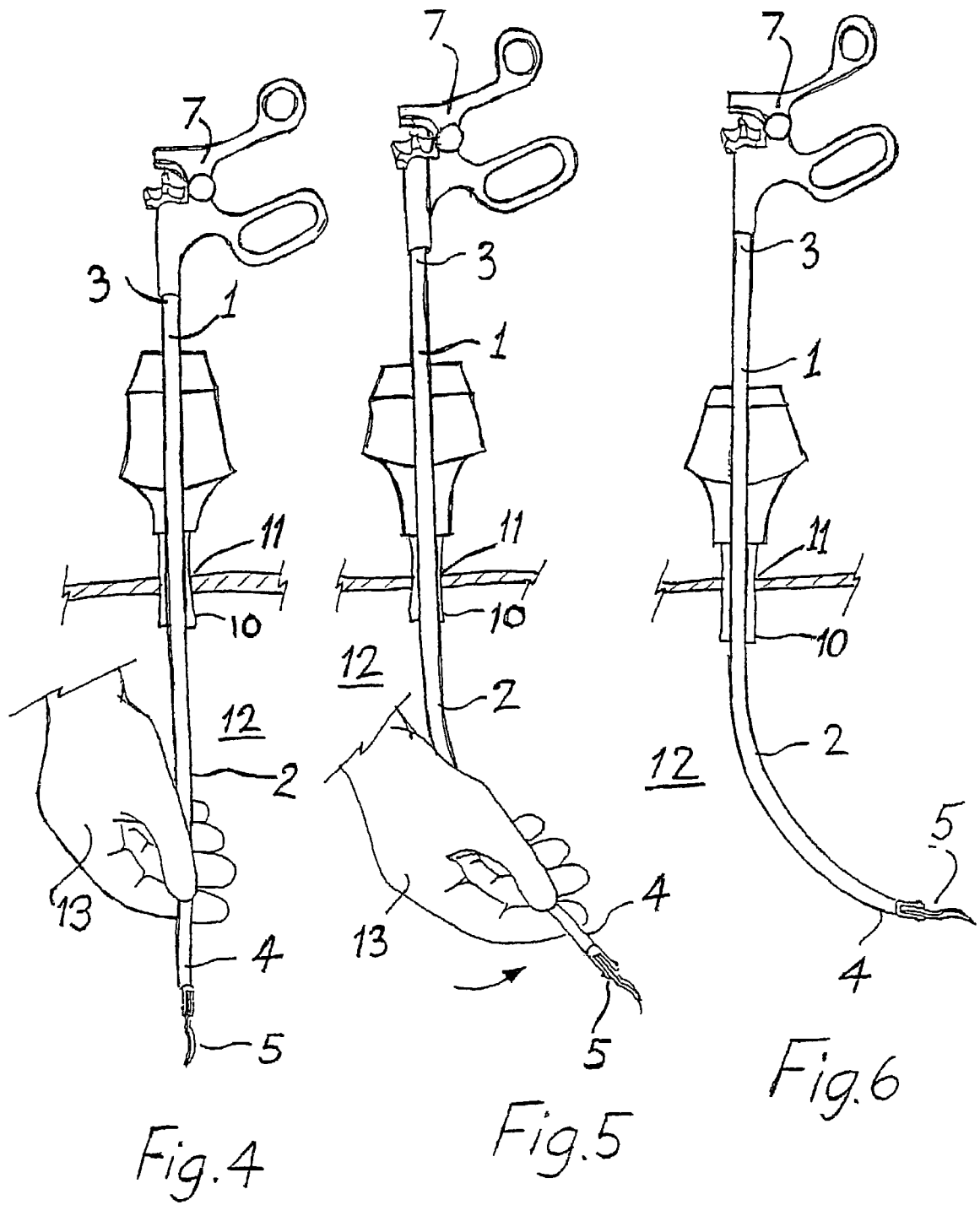

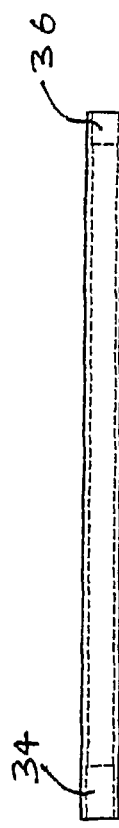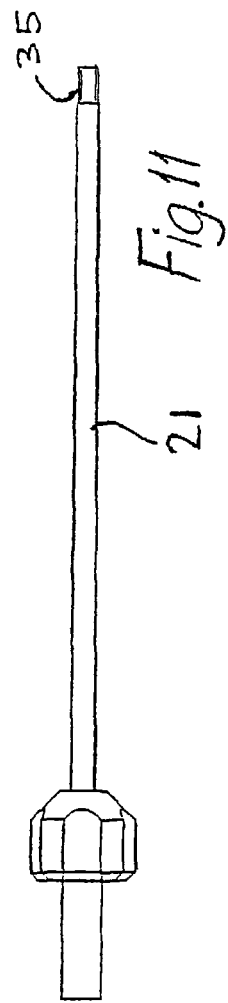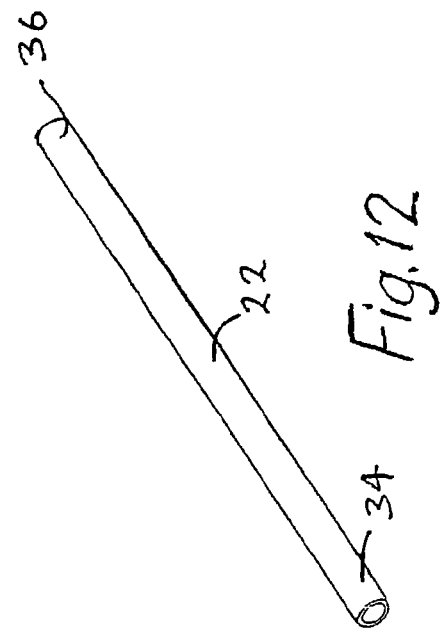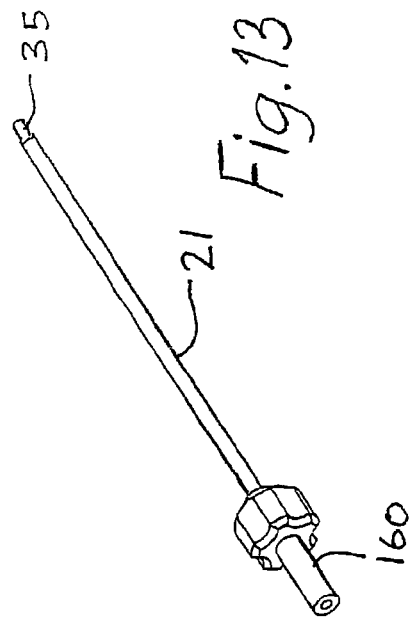

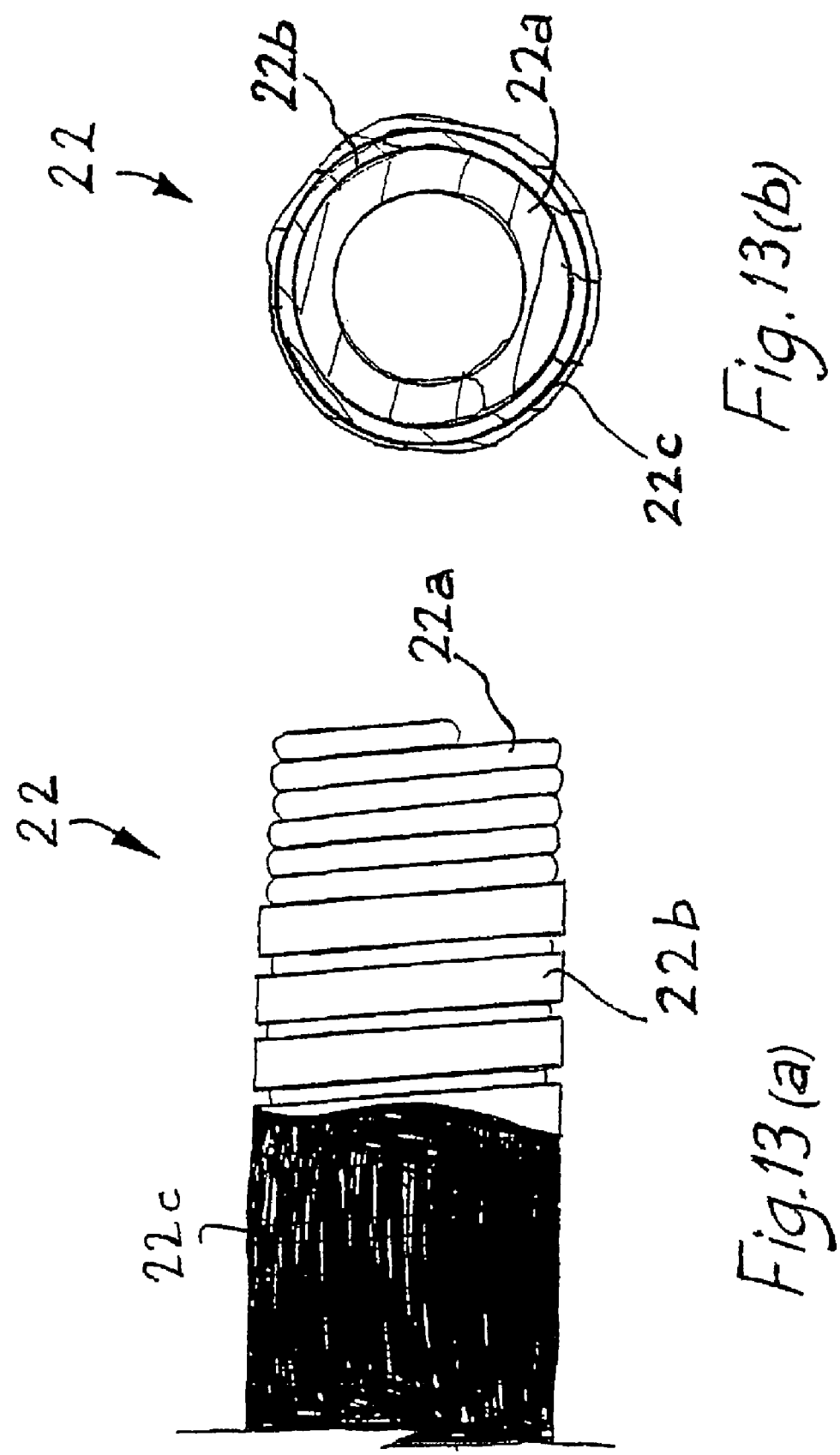

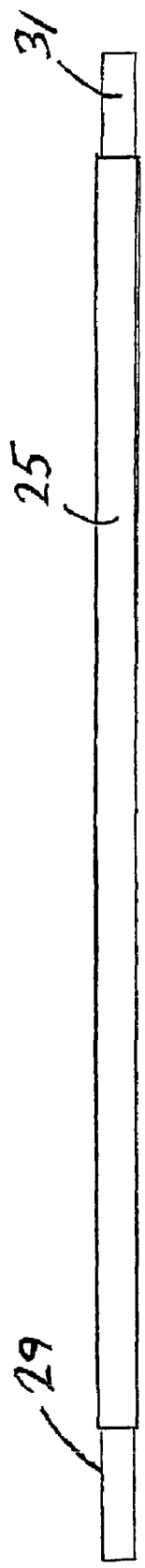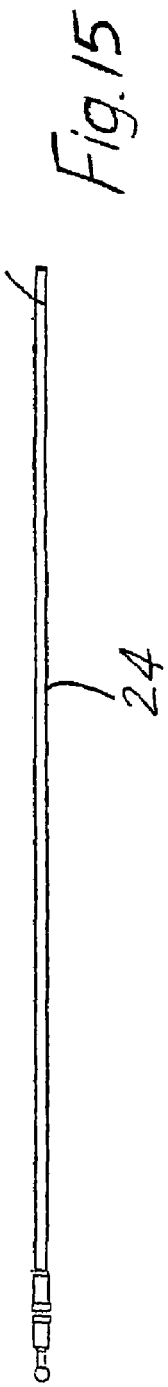

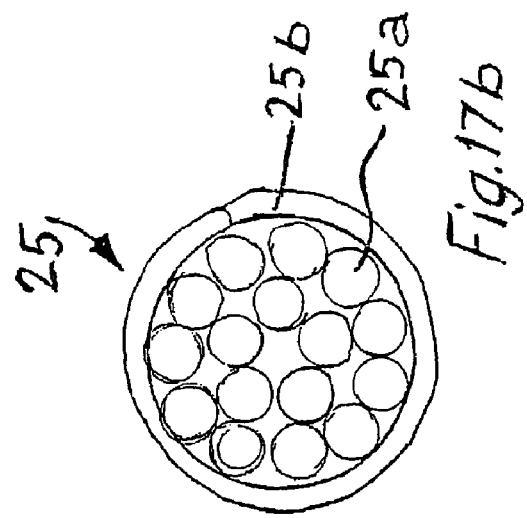
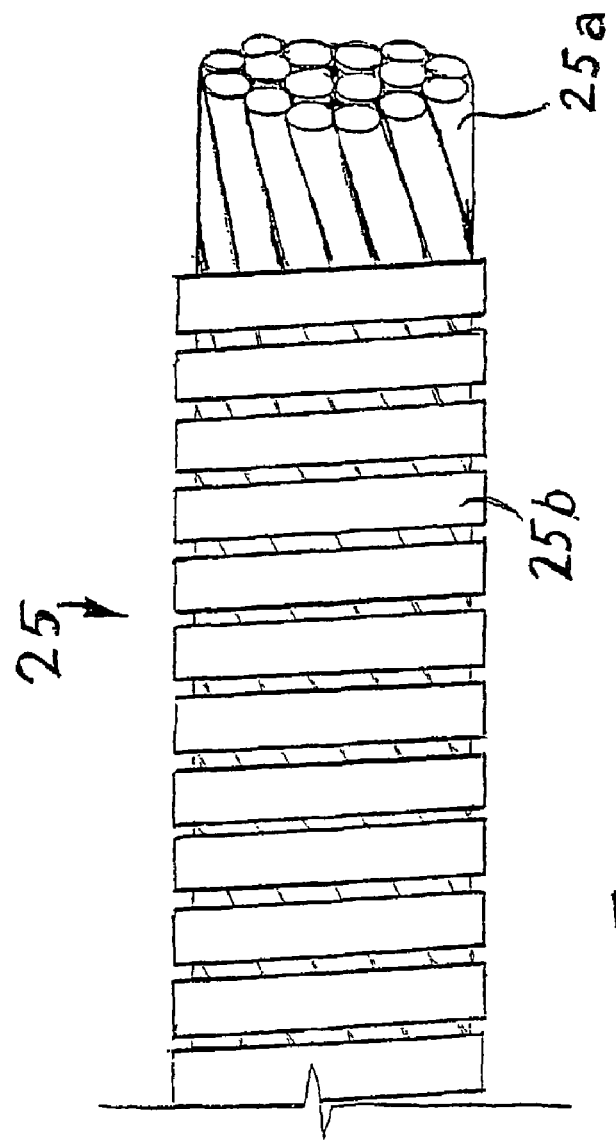
Fig.17b
Fig.17(a)

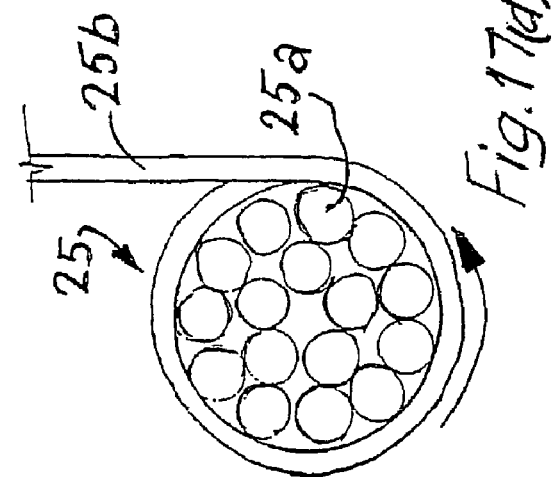
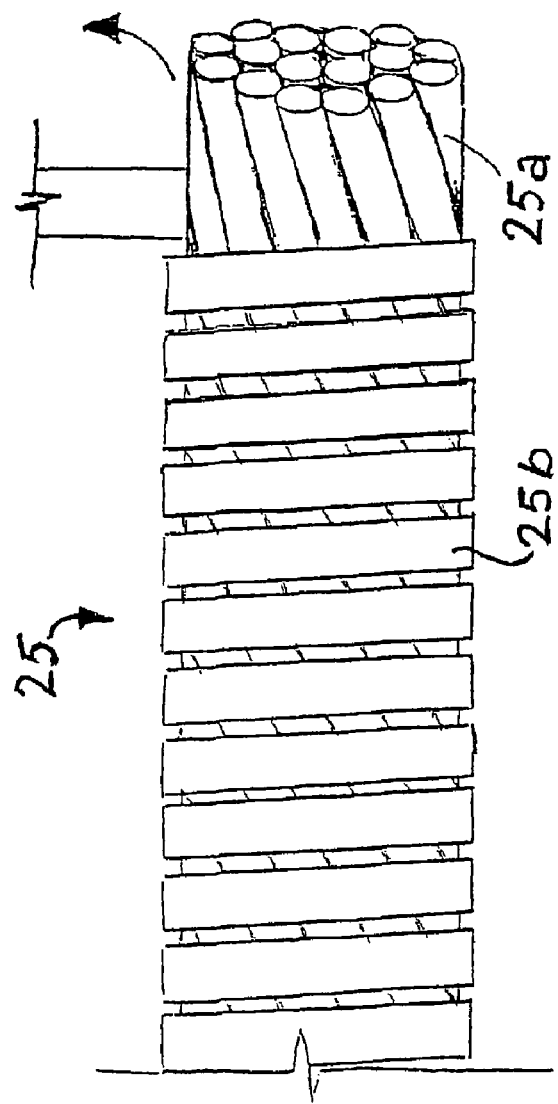

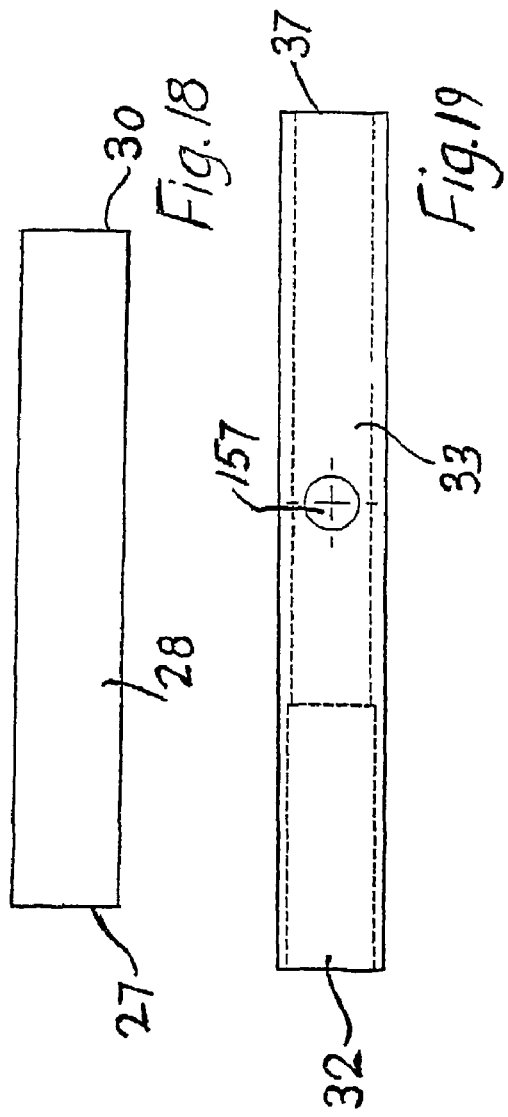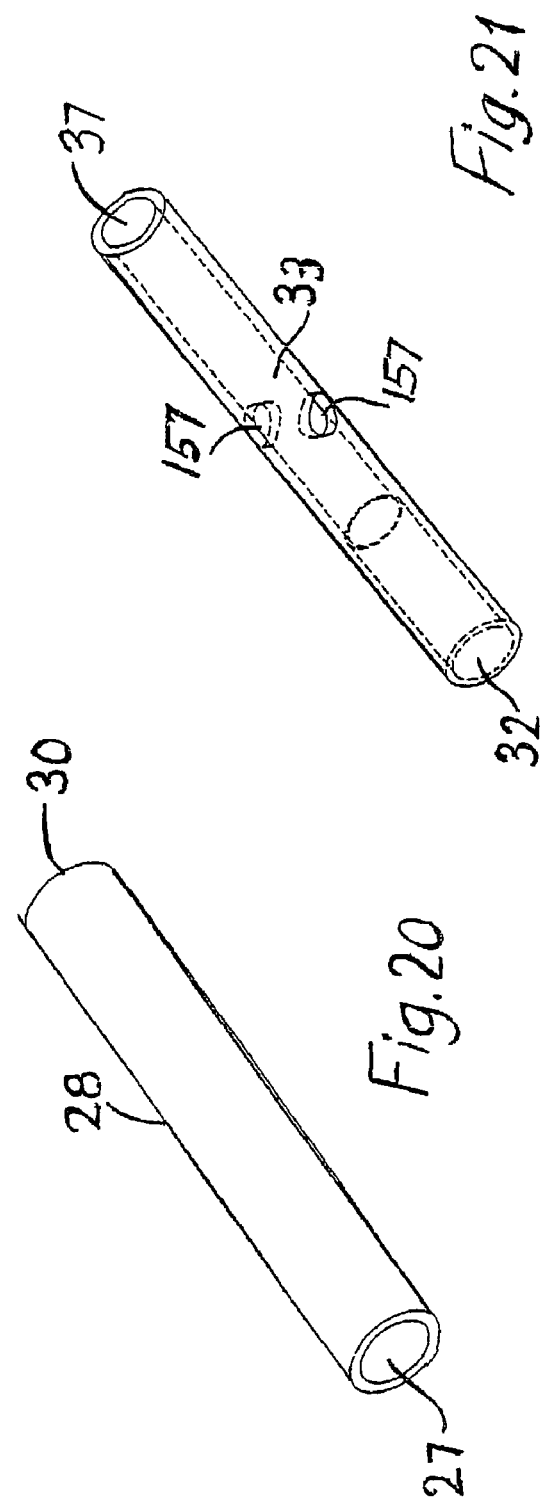

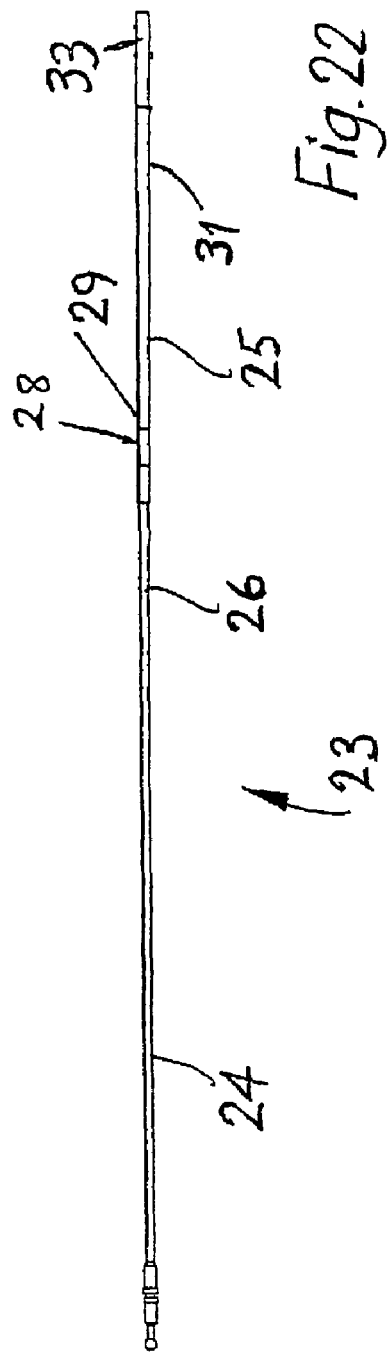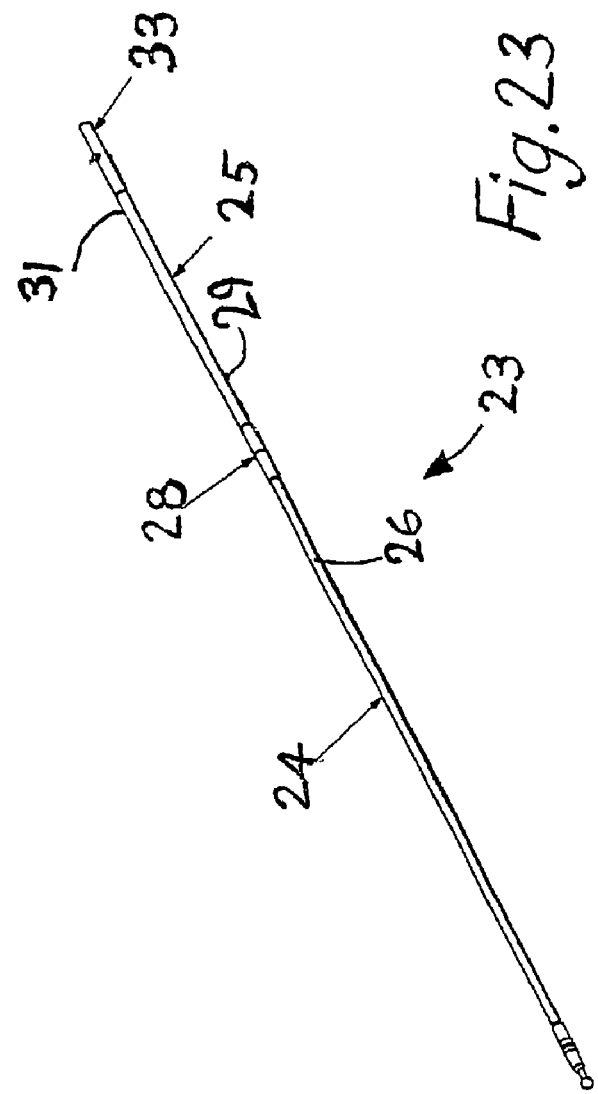
Fig. 22
Fig. 23

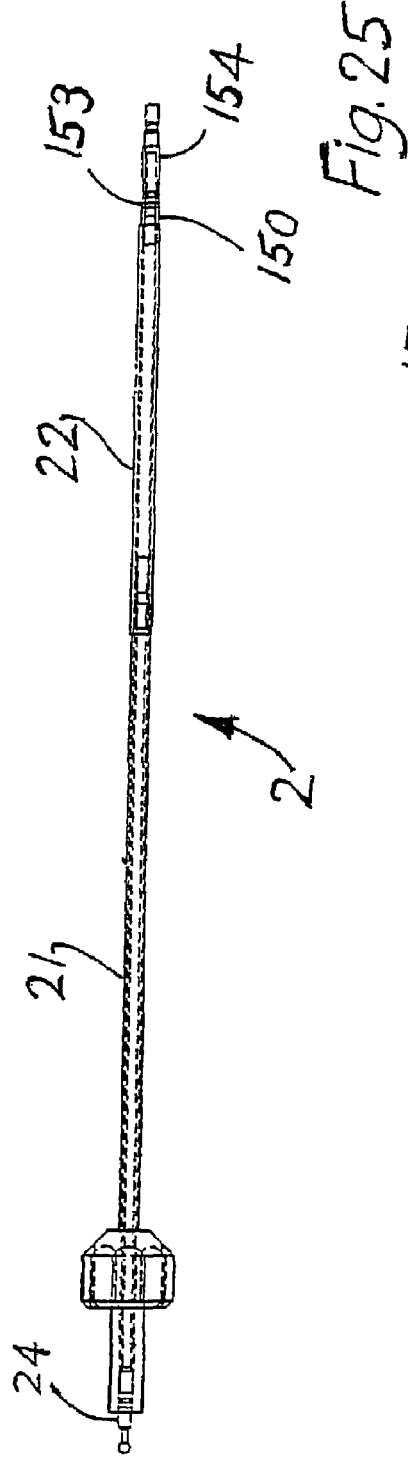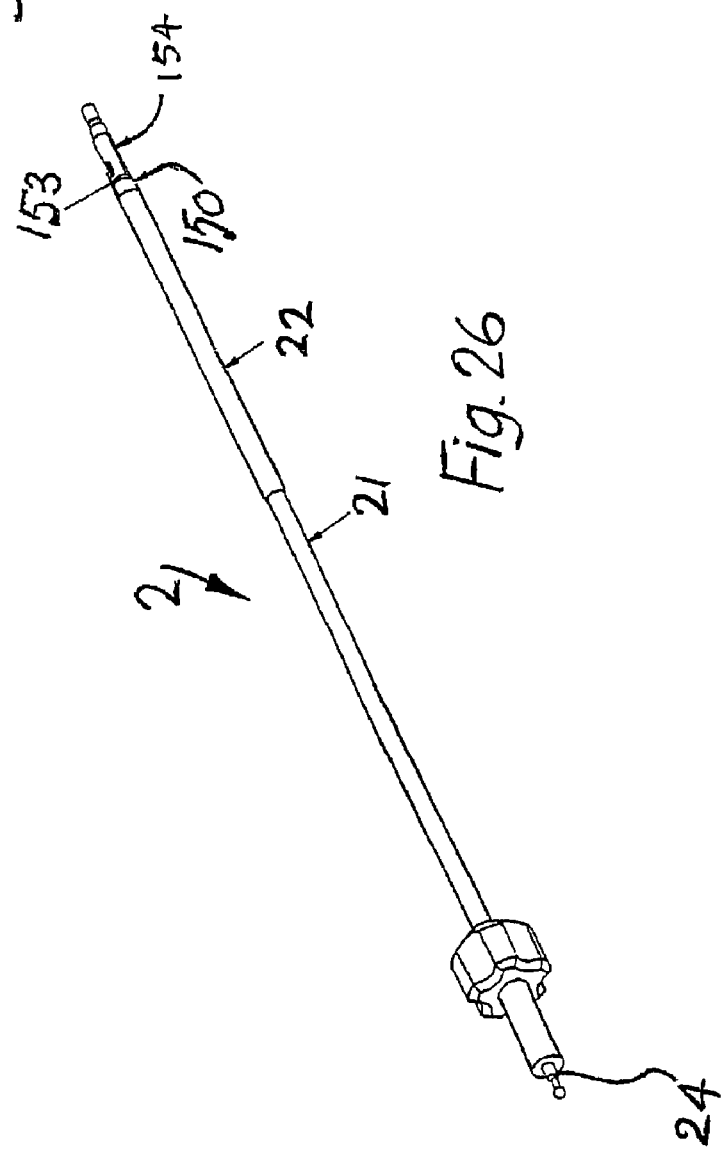

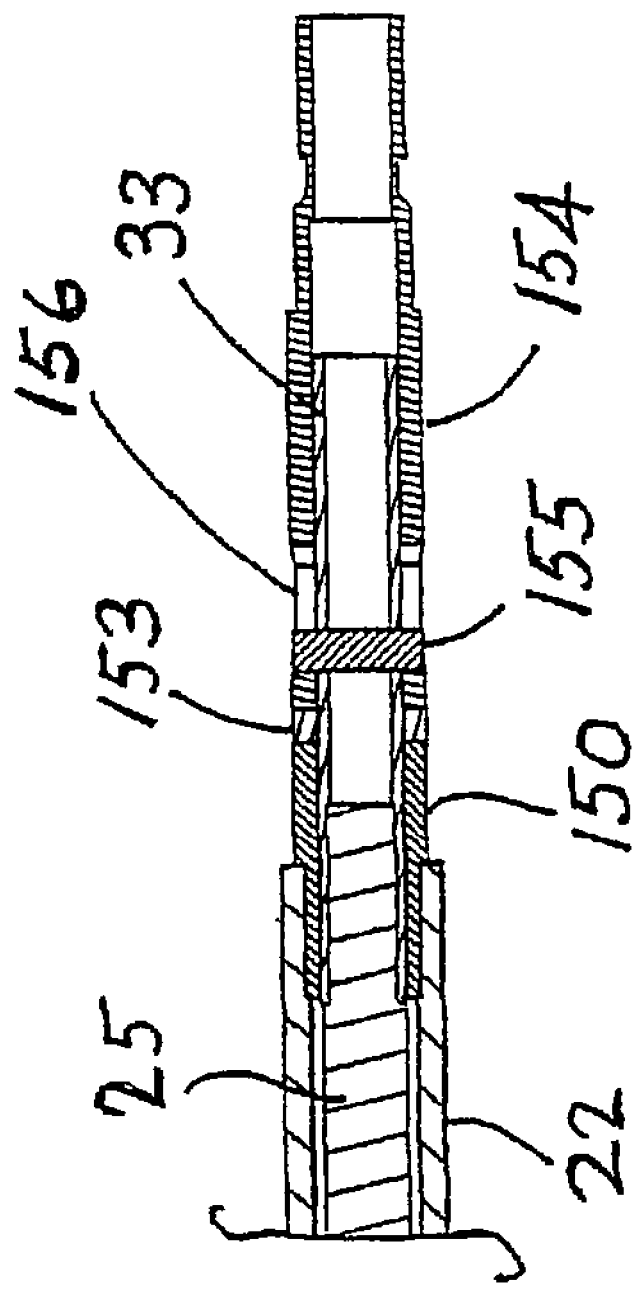

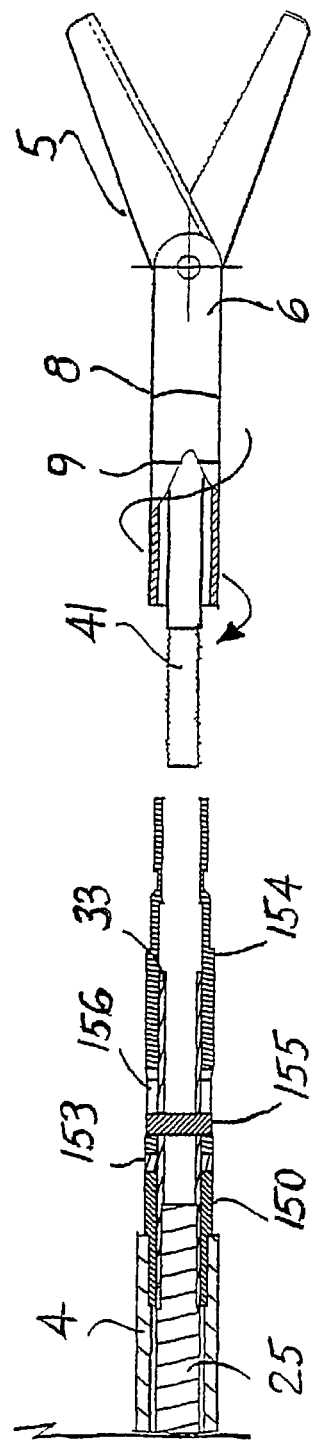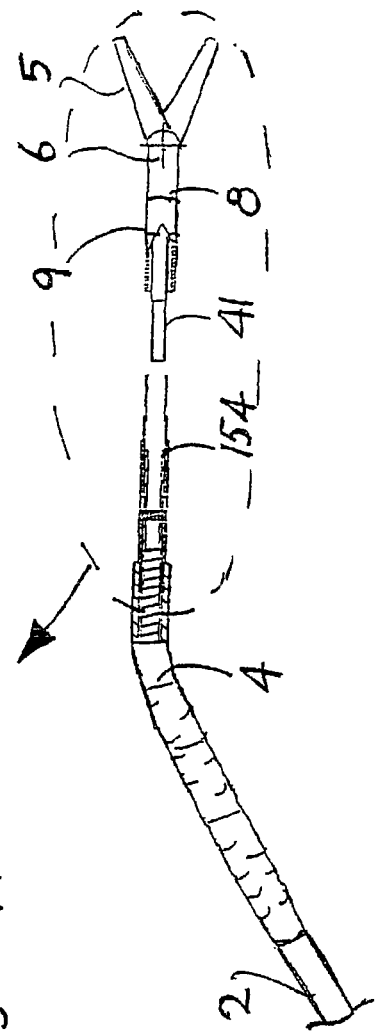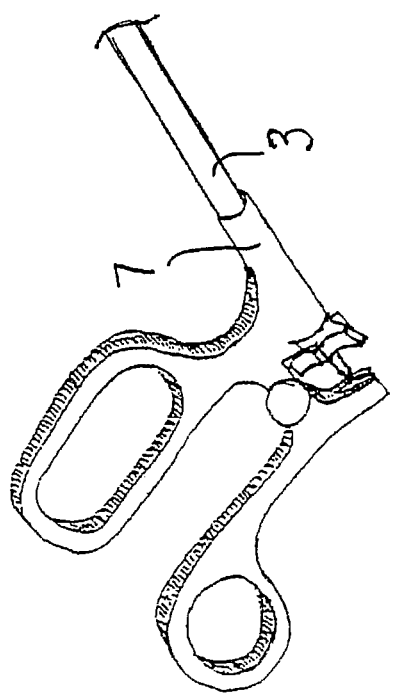
Fig.29(a)
Fig.29(b)

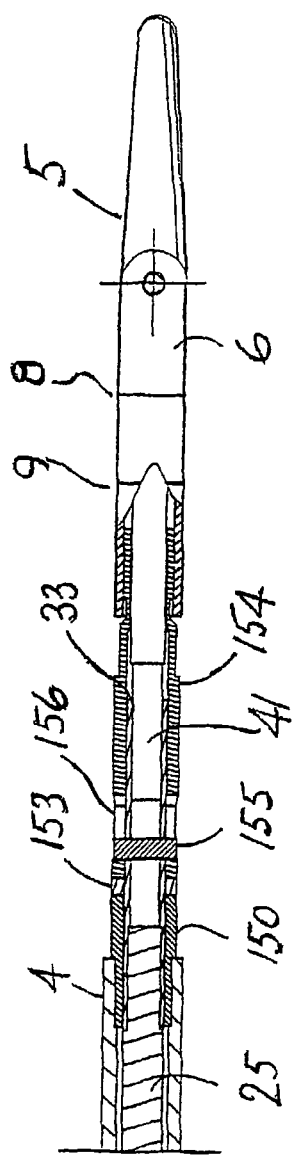
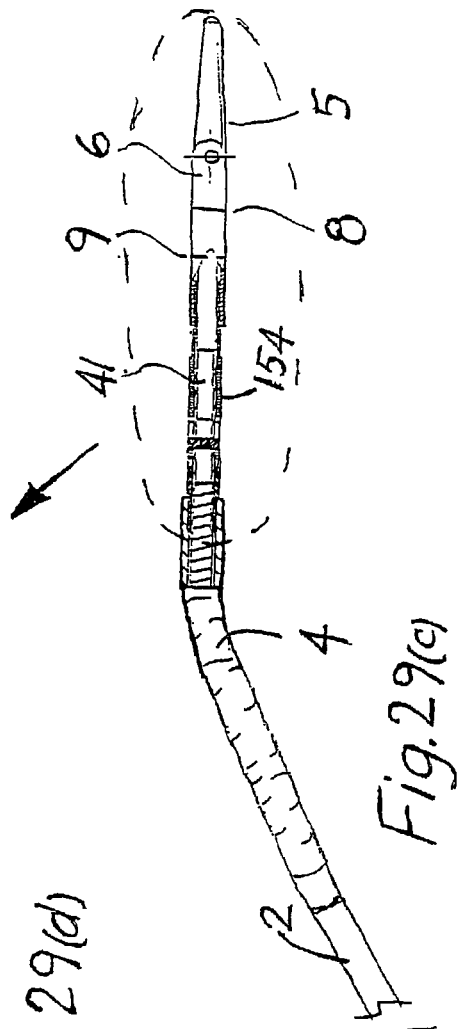
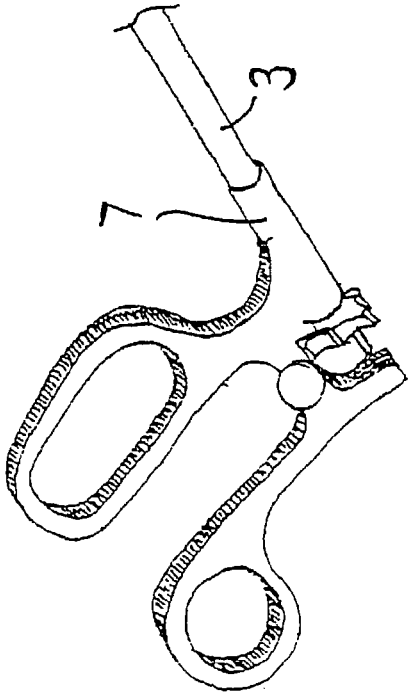
Fig. 29(c)
Fig. 29(d)

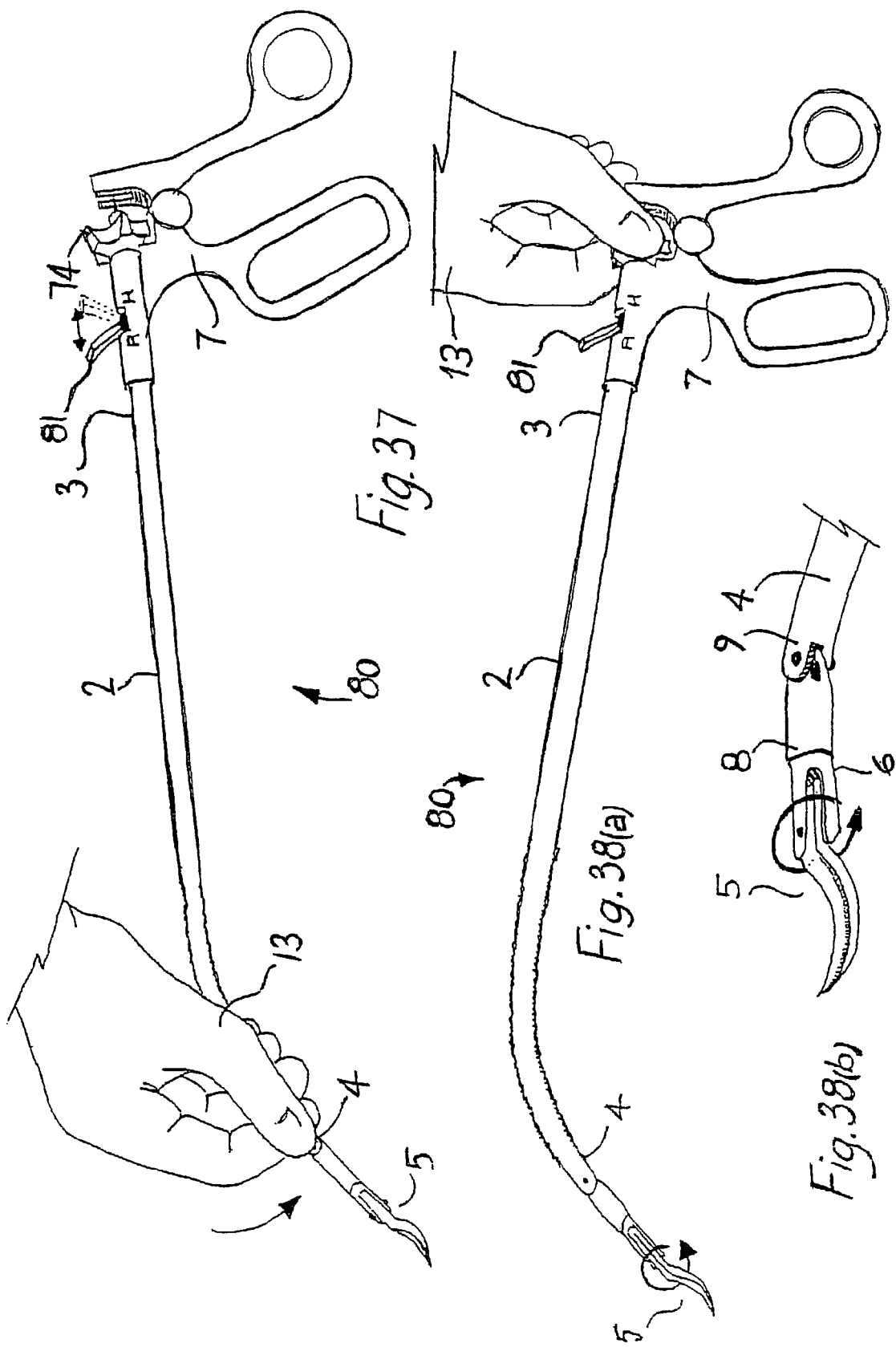

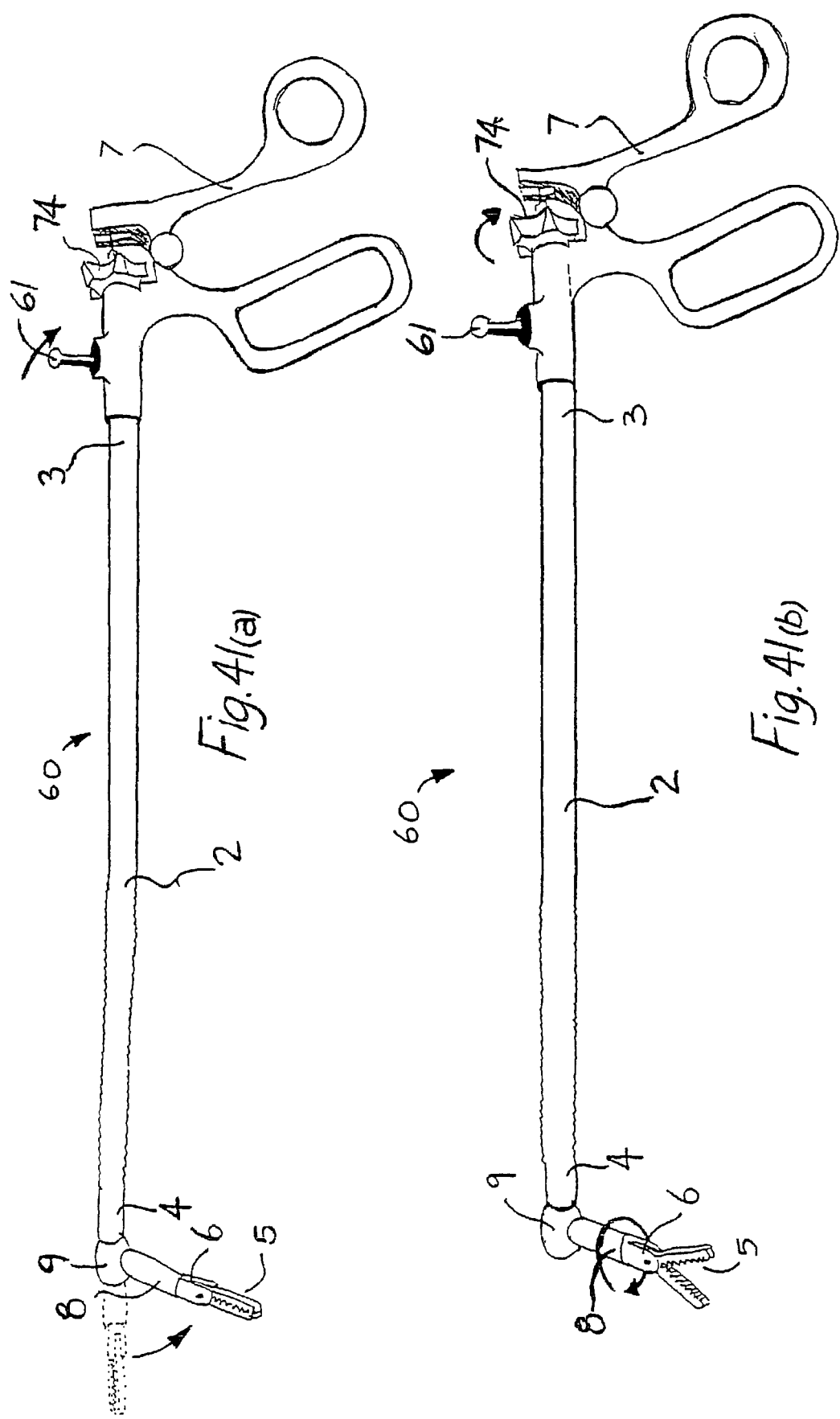

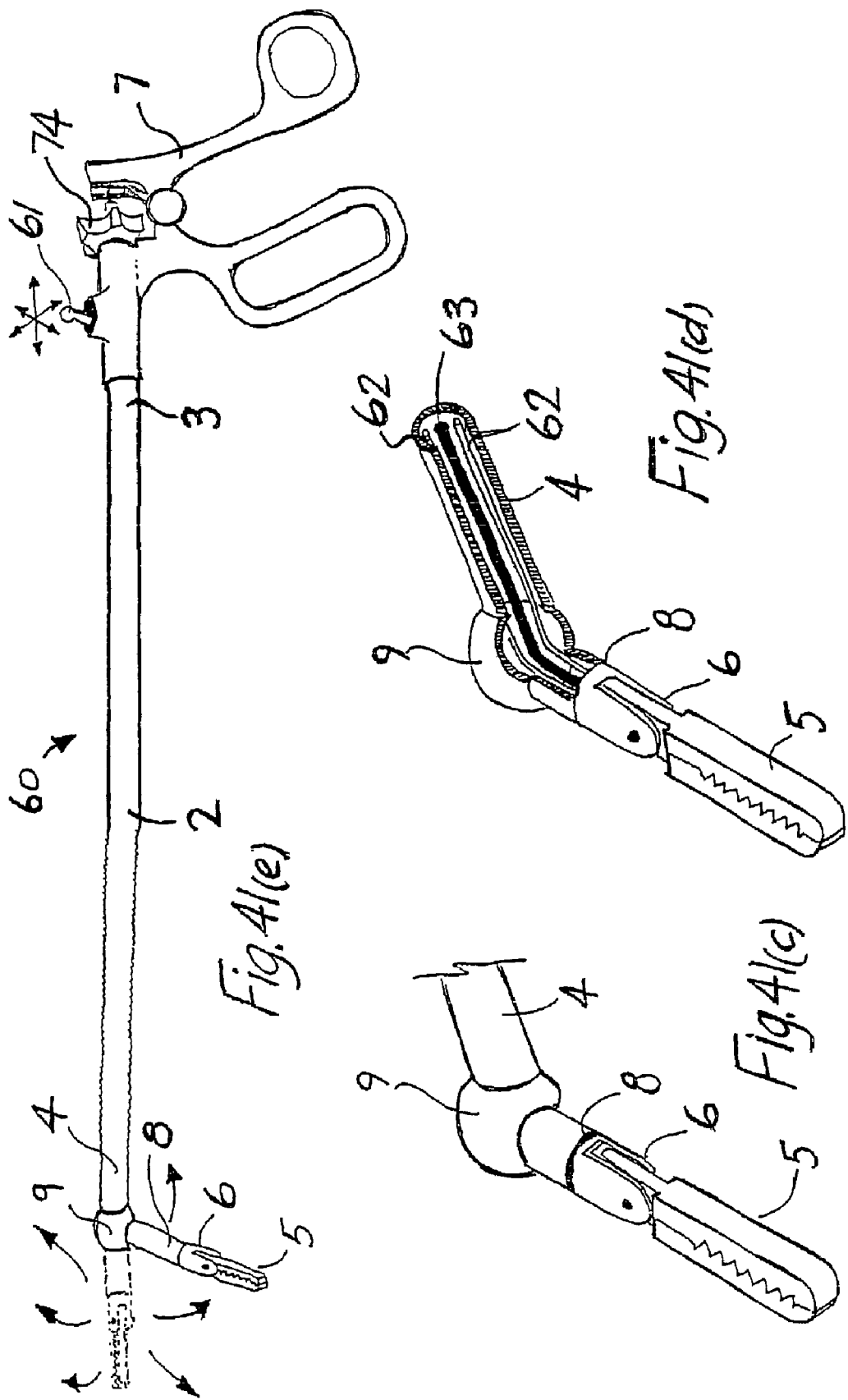

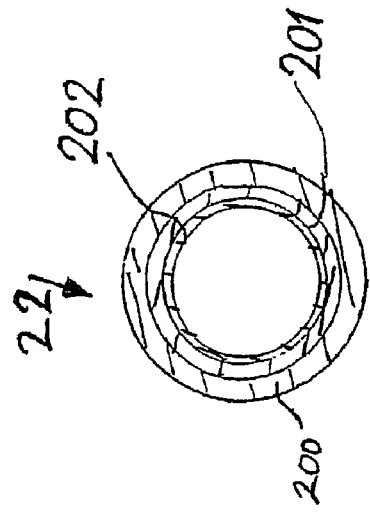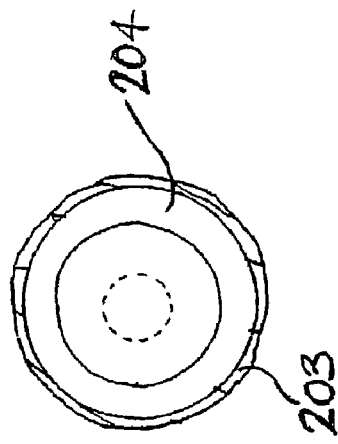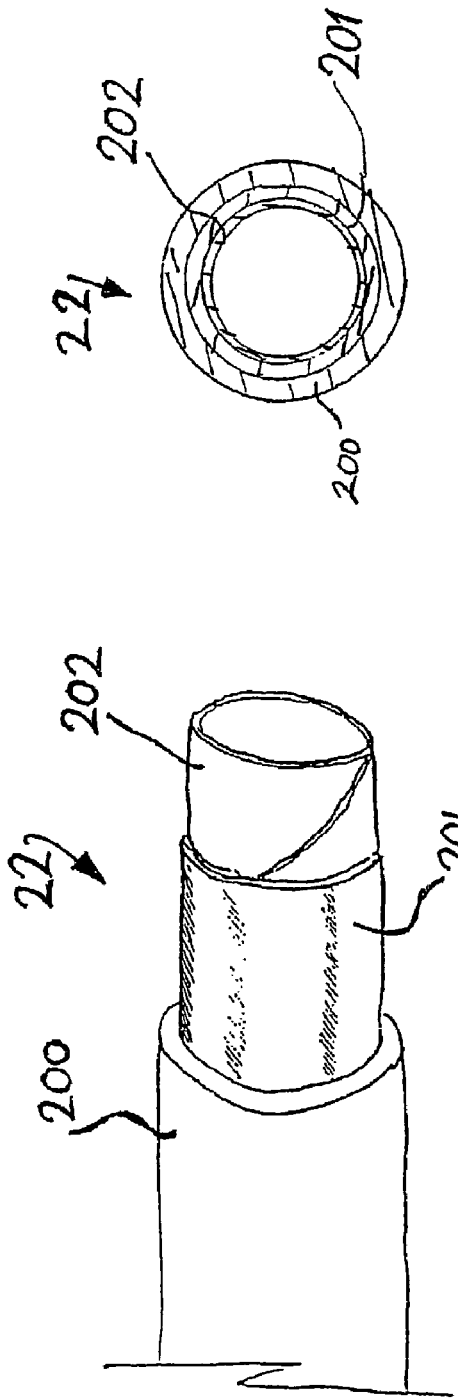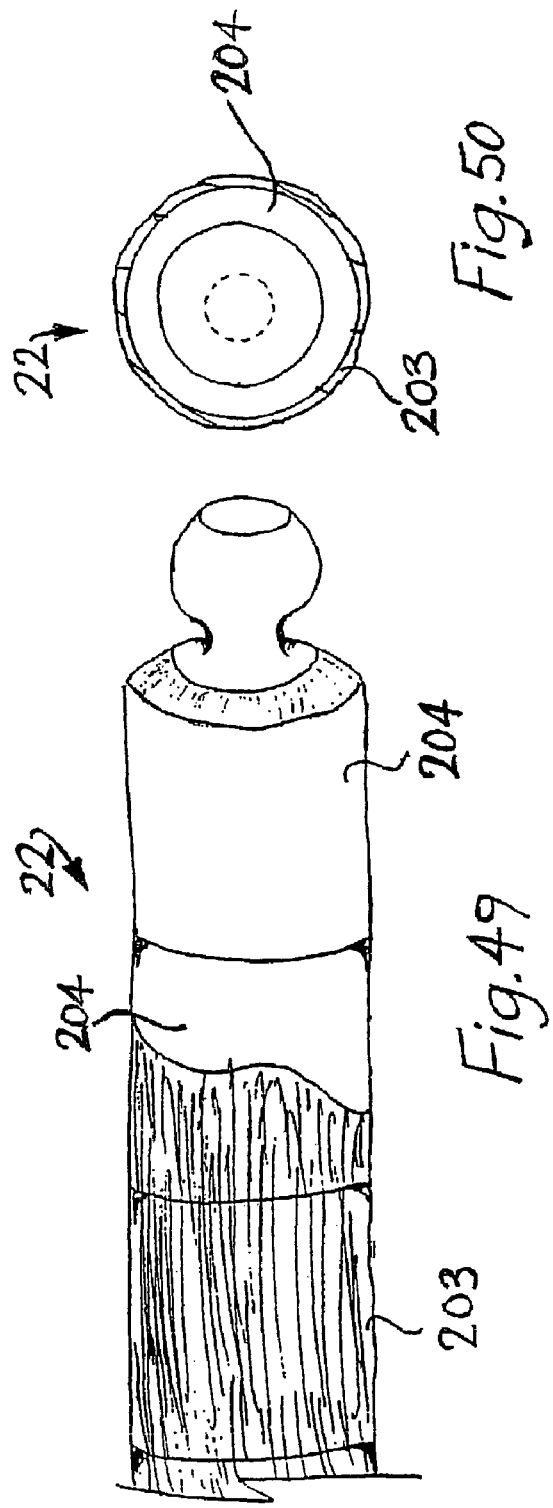

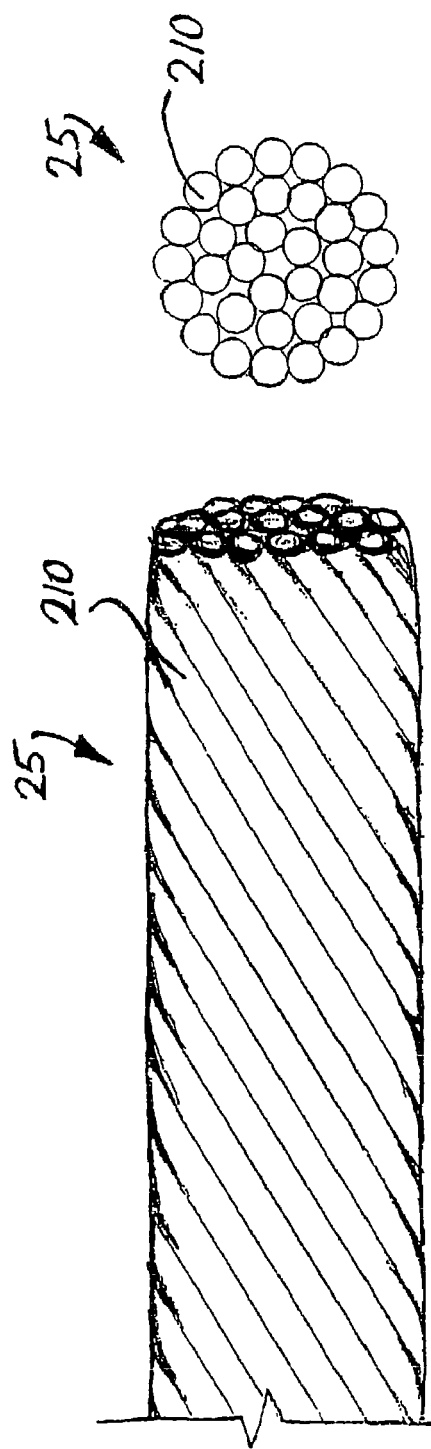
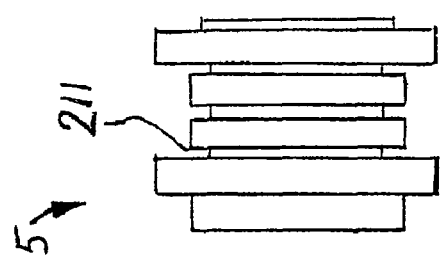
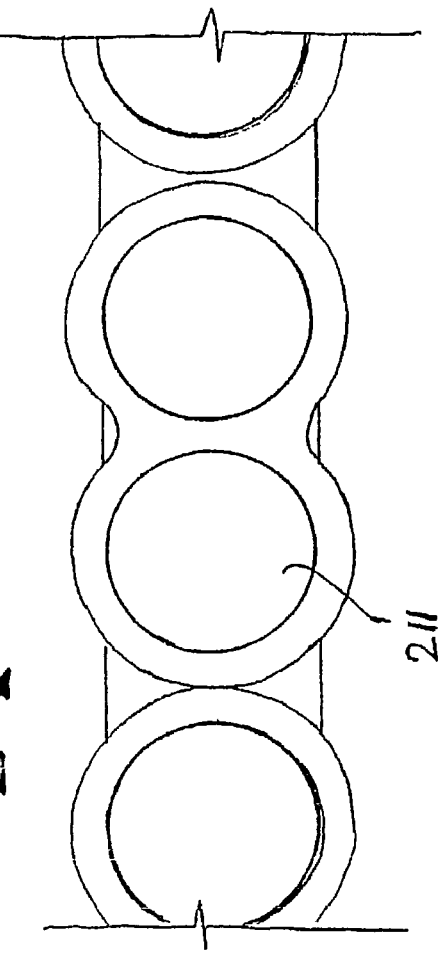

SURGICAL INSTRUMENT

CROSS REFERENCE RELATED APPLICATIONS

This application is a continuation of international application number PCT/IE01/00094, filed Jul. 23, 2001, and claims the priority of Ireland Patent Application No. 2000/0591, filed Jul. 21, 2000, Ireland Patent Application No. 2000/1072, filed Dec. 21, 2000, and Ireland Patent Application No. 2000/1061, filed Dec. 21, 2000 the contents of all of which are incorporated herein by reference.

INTRODUCTION

This invention relates to a minimally invasive surgical instrument and in particular to an instrument suitable for laparoscopic surgery, such as hand-assisted laparoscopy.

Conventional open surgery requires the creation of an incision in the abdominal wall to allow access to, and visualisation of internal organs and other anatomical structures. These incisions must be large enough to accommodate a surgeon's hands and any instruments to be utilised by the surgeon during the surgery. Traditionally the size of these incisions has been dictated by the need to see, retract and palpate internal bodily structures. While a large incision will provide access to the interior of the abdomen, such incisions are associated with long healing times, are susceptible to infection, and result in unsightly scars.

Surgical instruments for open surgery are known. For example, U.S. Pat. No. 6,139,563, describes a shaft member operatively coupled to a clamp-type tissue engaging means for use in a mini-laparotomy procedure. The instrument is suitable for insertion directly through an incision opening into an operating space, and the shaft is movable to maintain the opening uncluttered for direct visualisation of the operating space through the opening.

Laparoscopic surgery is an alternative to open surgery. In this method of surgery, the surgeon operates through very small incisions using remotely actuated instruments passed through the abdominal wall using a device called a cannula which creates a working channel. These working channels typically have a radial dimension in the range of from 2 to 15 millimetres. Vision is provided using a laparoscope which is typically 20 to 25 centimetres long and uses fibre-optic technology or a CCD camera to provide the operator with a picture of the interior of the abdomen. The abdomen is generally insufflated with a gas such as carbon dioxide or nitrogen to create a bubble effect and to provide a viable working space, known as the pneumoperitoneum, in which the operator may perform the surgery. Cannulae through which instruments are inserted are constructed to prevent loss of the insufflation gas through them, which would otherwise result in collapse of the pneumoperitoneum.

The benefits of laparoscopic surgery are numerous. Recovery times have been shown to be reduced due to the absence of a large incision. This has benefits for the patient, the healthcare organisation and society. The benefits to the patient are reduced stay in hospital, faster mobilisation and return to normal activity. The benefits to the health care organisation are also due to the reduced stay in hospital which is often the most expensive aspect of health care provision. Society benefits in faster return to work and normal activity of the patient.

Some surgical procedures are difficult to perform laparoscopically, for example surgery requiring the removal of large organ specimens, such as surgery for removal of the colon.

Laparoscopic surgical techniques are generally complex and surgeons tend to require long periods training to master these techniques. The surgeon manipulates organs and carries out delicate tasks using remotely actuated instruments. Because the surgeon is insulated from the material that he is working on, tactile feedback and the ability to palpate delicate structures is not possible.

The image viewed by the surgeon is a two dimensional image on a video screen, without three dimensional perspective of depth, and distance, and awareness of the proximity of other structures.

Recently, new surgical techniques have been developed that combine the advantages of both open surgery and laparoscopic surgery. In these new techniques, surgery is carried out using a laparoscopic approach with an additional, slightly larger incision to allow the surgeon to insert a hand into the insufflated abdomen. This is often referred to as hand-assisted laparpscopic surgery (HALS).

HALS allows surgeons to retain tactile feedback and three-dimensional perspective. It also permits rapid finger dissection, enhanced retraction capabilities and simplified haemostasis. There are several publications in the literature describing procedures carried out using a hand-assisted approach. These include total and sub-total colectomy, rectopexy, Nissen's fundoplication, gastrectomy, splenectomy, nephrectomy, pancreatectomy and others. Some of these procedures were previously performed using an open technique only.

During laparoscopy or HALS, a laparoscopic instrument is passed into an operating space through a laparoscopic cannula. The instrument is then moved into a desired position in the operating space. It is frequently desirable to approach an organ or piece of tissue in the operating space with the instrument in a particular desired orientation.

However, conventional laparoscopic instruments are difficult to manipulate as it is only possible to translate the instrument axially through the opening to the operating space, or to pivot the instrument about the opening.

In this way, the incision point restricts the degrees of freedom of the instrument, and make it difficult to approach an anatomical structure in a desired manner within the operating space. The restricted freedom of movement may require the surgeon to assume an uncomfortable position during the procedure leading to surgeon fatigue, and extended time periods to complete a procedure.

To access a desired position in the operating space and/or at a desired orientation in the operating space with the instrument, it may be necessary to create another opening to the operating space and to pass the instrument through a cannula at this other opening into the operating space. This causes further trauma to the patient.

Floppy surgical instruments are also known. For example, U.S. Pat. No. 5,779,727 discloses a surgical scissors at the end of a flexible arm for use in laparoscopic surgery. Such floppy instruments restrict the surgeon's freedom of movement as the surgeon must hold the floppy instrument in a desired position and/or at a desired orientation in the operating space throughout the laparoscopic procedure.

There is therefore a need for a minimally invasive surgical instrument which will facilitate access to a desired site in an opening into an operating space without restricting the freedom of movement of a surgeon.

STATEMENTS OF INVENTION

According to the invention, there is provided a minimally invasive surgical instrument comprising:— an elongate stem extending between a proximal end for location externally of an operating space and a distal end for insertion into an operating space;

an end effector at the distal end of the stem, the end effector comprising a proximal main body;

at least portion of the stem being malleable to facilitate manipulation and to maintain the stem in a manipulated position and/or orientation within the operating space; and at least one joint for independent movement of the end effector main body relative to the distal end of the stem.

In one embodiment of the invention the joint facilitates rotation of the end effector main body about a longitudinal axis of the end effector relative to the distal end of the stem.

In another embodiment of the invention the joint facilitates pivoting of the end effector main body relative to the distal end of the stem. In one case the joint comprises a universal joint. In another case the pivotal joint comprises a ball-and-socket joint. In a further case the joint comprises a hinge.

Preferably the instrument comprises a rotational joint and a pivoting joint. Ideally the rotational joint is distal of the pivoting joint.

In a preferred embodiment the stem has a distal portion adjacent the distal end of the stem, and the distal portion of the stem is malleable.

In one case the stem is malleable substantially along the length thereof.

In a preferred case the stem has an intermediate portion intermediate the proximal end of the stem and the distal end of the stem, and the intermediate portion of the stem is rigid.

The malleability of the malleable portion of the stem may vary along the length of the malleable portion of the stem.

In a particulary preferred embodiment the stem comprises at least one seal to prevent leakage of gas through the stem. The seal may be provided by a gas-tight sealing jacket around the malleable portion of the stem.

In one case the stem comprises an outer shaft and an inner elongate member. Preferably the seal is provided between the outer shaft and the inner elongate member. Ideally the seal comprises an O-ring.

The inner member may be at least partially flexible. The inner member may be at least partially rigid. Most preferably a proximal portion of the inner member is rigid and a distal portion of the inner member is flexible.

In another embodiment at least portion of the stem is of a layered construction. Ideally at least one layer acts as a seal. Most preferably at least one layer comprises a spring coil. In another case at least one layer is a coil braid. At least one layer may be of a polymeric material. Ideally the polymeric material is polyvinylchloride.

At least one layer may be of a metallic material. Ideally the metallic material is aluminium.

In another embodiment at least portion of the stem is of a linkage construction. Preferably the inks are interconnected by hinges.

In a preferred case the end effector main body is mounted to the distal end of the stem. Ideally the joint is provided in the region of mounting of the end effector main body to the distal end of the stem.

In one embodiment the end effector main body is releasably mounted to the distal end of the stem. Preferably the end effector main body is threadably mounted to the distal end of the stem.

The instrument may comprise a lock to selectively prevent demounting of the end effector main body from the distal end of the stem. The lock preferably comprises a lip for engagement in a recess to limit movement of the end effector main body relative to the stem. The end effector main body may comprise the lip and the recess may be defined on the stem. Preferably the lip is movable between a first position engaged in the recess and a second disengaged position. Ideally the recess is sized to facilitate up to 360° rotation of the end effector main body relative to the distal end of the stem without demounting the end effector main body from the distal end of the stem.

In another embodiment the end effector main body is fixedly mounted to the distal end of the stem. Ideally the end effector main body is mounted to the distal end of the stem by an engagement of at least one male projection in at least one corresponding female recess.

In another preferred embodiment the instrument comprises a mover to facilitate independent movement of the end effector main body relative to the distal end of the stem from the proximal end of the stem.

The instrument preferably comprises a manipulator to facilitate manipulation of the position and/or orientation of the stem from the proximal end of the stem.

Desirably the instrument comprises a lock to lock the stem in a desired manipulated position and/or orientation.

The mover and/or the manipulator and/or the lock may be provided by at least one wire extending along at least portion of the stem. Ideally the wire is coupled to the end effector. The wire may be releasbly coupled to the end effector. Preferably the wire is threadably coupled to the end effector.

The wire may be fixedly coupled to the end effector. Preferably the wire is coupled to the end effector by an engagement of at least male projection in at least one corresponding female recess.

In a preferred embodiment the wire is slidably received in at least one guide on the stem. Ideally the wire comprises a stop to limit movement of the wire.

Desirably the stem has a proximal portion adjacent a proximal end of the stem, and the proximal portion of the stem is flexible.

In another embodiment of the invention the stem is extendable from a retracted configuration to an extended configuration. The stem may be telescopically extendable. The stem may be extendable in a concertina manner.

In one embodiment the end effector main body comprises an orientation indicator. Preferably the indicator is provided by a knurled or ridged portion of the end effector.

In another aspect, the invention provides a surgical apparatus comprising a minimally invasive surgical instrument of the invention and a cannula through which the instrument may be partially inserted.

The cannula may be at least partially flexible. Ideally a distal portion of the cannula adjacent a distal end of the cannula is flexible.

According to a further aspect of the invention, there is provided a method of performing minimally invasive surgery comprising the steps of:— providing a surgical instrument, the instrument having a proximal end and a distal end, and at least portion of the instrument being malleable;

partially inserting the instrument through an opening into an operating space so that the proximal end is located externally of the operating space and the distal end is located within the operating space; and manipulating the instrument into a desired position and/or orientation, the manipulated position and/or orientation being maintained by the malleable nature of the instrument.

In one embodiment of the invention the instrument comprises an end effector at the distal end of the instrument, the end effector comprising a proximal main body and a distal operator, and the method comprises the step of moving the end effector main body in at least one direction independently relative to the distal end of the instrument. Ideally the end effector main body is rotated about a longitudinal axis of the end effector relative to the distal end of the instrument.

The end effector main body is preferably pivoted relative to the distal end of the instrument in at least one direction.

The instrument may be at least partially manipulated before partial insertion of the instrument into the operating space.

The instrument may be at least partially manipulated after partial insertion of the instrument into the operating space.

The instrument may be at least partially manipulated during partial insertion of the instrument into the operating space. Ideally the instrument is at least partially manipulated by levering the proximal end of the instrument about the opening to the operating space when the instrument is partially inserted through the opening to the operating space.

In one preferred case the instrument is at least partially manipulated from the proximal end of the instrument externally of the operating space. The method may comprise the step of inserting a hand into the operating space. Ideally the method comprises the steps of:—
  providing a hand access device;
  mounting the hand access device at an opening to the operating space; and
  inserting the hand through the hand access device into the operating space.

In another preferred case the instrument is at least partially manipulated by the hand from within the operating space.

In one case the end effector main body is at least partially moved relative to the distal end of the instrument from the proximal end of the instrument externally of the operating space.

In another case the end effector main body is at least partially moved relative to the distal end of the instrument by the hand from within the operating space.

Desirably the method comprises the step of mounting the end effector main body to the distal end of the instrument. Ideally the end effector main body is mounted to the distal end of the instrument within the operating space. Alternatively the end effector main body may be mounted to the distal end of the instrument externally of the operating space.

In a preferred embodiment the method comprises the step of locking the instrument in the manipulated position and/or orientation.

In another case the method comprises the step of extending the instrument from a retracted configuration to an extended configuration.

In another preferred embodiment of the invention the method comprises the steps of:—
  providing a cannula;
  partially inserting the cannula through the opening to the operating space; and
  partially inserting the instrument through the cannula into the operating space.

The invention provides in one case a method of performing minimally invasive abdominal surgery wherein the operating space is an abdominal cavity.

The invention provides in another case a method of performing laparoscopy.

Another aspect of the invention provides a laparoscopic surgical instrument comprising:—
  an elongate stem extending between a proximal end for location externally of an operating space and a distal end for insertion into an operating space;
  the stem comprising at least one seal for gas-tight insertion of the stem through an opening to an operating space to maintain pneumoperitoneum in the operating space; and
  at least portion of the stem being malleable to facilitate manipulation in an operating space and to maintain the stem in a manipulated position and/or orientation within the operating space.

The seal may be provided at the malleable portion of the stem.

In one case the seal comprises a gas-tight sealing jacket.

In another case the seal comprises an O-ring.

In a further aspect of the invention, there is provided a minimally invasive surgical instrument comprising:—
  an elongate stem extending between a proximal end for location externally of an operating space and a distal end for insertion into an operating space; and
  an end effector at the distal end of the stem;
  the end effector having a low-profile, introduction configuration, the radial dimension of the end effector at least in the introduction configuration being in the range of from 2 mm to 15 mm;
  at least portion of the stem being malleable to facilitate manipulation in the operating space and to maintain the stem in a manipulated position and/or orientation within the operating space.

Ideally the end effector is mounted to the distal end of the stem.

According to yet another aspect, the invention provides a minimally invasive surgical instrument comprising:—
  an elongate stem extending between a proximal end for location externally of an operating space and a distal end for insertion into an operating space;
  the stem having means for mounting of an end effector at the distal end of the stem;
  the radial dimension of the stem being in the range of from 2 mm to 15 mm; and
  at least portion of the stem being malleable to facilitate manipulation in the operating space and to maintain the stem in a manipulated position and/or orientation within the operating space.

In one case, the invention provides a laparoscopic surgical instrument.

In a further aspect of the invention, there is provided a coupling device to selectively prevent demounting of a first shaft releasably mounted to a second shaft, the device comprising a lip on the first shaft for engagement in a recess on the second shaft to limit movement of the first shaft relative to the second shaft.

The lip may be slidable along the first shaft between a first position engaged in the recess and a second disengaged position.

Ideally the recess is sized to facilitate up to 360° rotation of the first shaft relative to the second shaft without demounting the first shaft from the second shaft.

The malleable nature of the surgical instrument according to the invention enables the distal end of the instrument to be easily manipulated into a desired position and/or orientation within the operating space. This provides the surgeon using the instrument with the freedom to access sites in the operating space remote from an opening to the operating space. Most importantly, the instrument maintains this position without requiring the surgeon to hold the instrument in the manipulated position and/or orientation.

The end effector at the distal end of the instrument can be moved relative to the distal end of the instrument. This enhances the degrees of freedom of the instrument by enabling the end effector to pivot, and/or to rotate, and/or to move in any other suitable manner very close to a site of interest in the operating space for carrying out a desired surgical procedure.

The joint enables degrees of freedom movement for the end effector due to the short radius of rotation.

The surgical instrument of the invention is particularly applicable to hand assisted surgery and in particular to surgical techniques in which an opening is formed in the abdomen, a sealing hand access device is placed in the opening and a surgeon's hand is then inserted through the hand access device into the operating space for carrying out procedures in the operating space. One such sealing device is described in our International patent application published under number WO-A-00/32117, the entire contents of which are incorporated herein by reference. The sealing device seals to the wound edge and to a surgeon's arm to maintain pneumoperitoneum in the operating space.

In this case a surgical instrument is inserted through a cannula into the operating space and the position and/or orientation of the distal end of the instrument is controlled by the surgeon's hand. The end effector can also be moved relative to the distal end of the instrument by the surgeon's hand to carry out a desired surgical procedure within the operating space.

It will be appreciated that another laparoscopic instrument may be used alternatively or additionally to the surgeon's hand to manipulate the instrument and/or to move the end effector relative to the distal end of the instrument.

BRIEF DESCRIPTION OF THE DRAWINGS

The invention will be more clearly understood from the following description of some embodiments thereof, given by way of example only, with reference to the accompanying drawings, in which:—

FIG. 4 is a schematic view of the instrument of FIG. 1 partially inserted through a cannula into an operating space;

FIG. 5 is a schematic view illustrating manipulation of the instrument of FIG. 4 within the operating space;

FIG. 6 is a schematic view of the instrument of FIG. 5 after manipulation;

FIG. 10 is a side view of a malleable tube part of the instrument of FIGS. 1 to 9;

FIG. 11 is a side view of a rigid tube part of the instrument of FIGS. 1 to 9;

FIG. 12 is a perspective view of the tube of FIG. 10;

FIG. 13($a$) is a side, partially cross-sectional view of the tube of FIG. 10;

FIG. 13($b$) is an end view of the tube of FIG. 13($a$);

FIGS. 13($c$) and 13($d$) are views similar to FIGS. 13($a$) and 13($b$) illustrating formation of the tube of FIGS. 13($a$) and 13($b$);

FIG. 14 is a side view of a flexible cable part of the instrument of FIGS. 1 to 9;

FIG. 15 is a side view of a rigid rod part of the instrument of FIGS. 1 to 9;

FIG. 16 is a perspective view of the cable of FIG. 14;

FIG. 17 is a perspective view of the rod of FIG. 15;

FIG. 17($a$) is a side, partially cross-sectional view of the cable of FIG. 14;

FIG. 17($b$) is an end view of the cable of FIG. 17($a$);

FIGS. 17($c$) and 17($d$) are views similar to FIGS. 17($a$) and 17($b$) illustrating formation of the cable of FIGS. 17($a$) and 17($b$);

FIG. 18 is a side view of a first coupling tube part of the instrument of FIGS. 1 to 9;

FIG. 19 is a side view of a second coupling tube part of the instrument of FIGS. 1 to 9;

FIG. 20 is a perspective view of the first coupling tube of FIG. 18;

FIG. 21 is a perspective view of the second coupling tube of FIG. 19;

FIG. 22 is a side view of an inner elongate member part of the instrument of FIGS. 1 to 9;

FIG. 23 is a perspective view of the inner elongate member of FIG. 22;

FIG. 24($b$) is a perspective view of the spacer element of FIG. 24 ($b$);

FIG. 24($c$) is a side view of a spring washer part of the instrument of FIGS. 1 to 9;

FIG. 24($d$) is a perspective view of the spring washer of FIG. 24($c$);

FIG. 24($e$) is a side view of an end effector connector piece of the instrument of FIGS. 1 to 9;

FIG. 24($f$) is a perspective view of the end effector connector piece of FIG. 24($e$);

FIGS. 25 and 26 are side and perspective views respectively of the inner elongate member of FIG. 22 inserted through an outer shaft part of the instrument of FIGS. 1 to 9;

FIG. 27 is an enlarged, side view of part of the assembly of FIGS. 25 and 26;

FIGS. 29($a$) to 29($d$) are schematic, partially cross-sectional views illustrating mounting of the end effector to a distal end of the instrument of FIGS. 1 to 28;

FIG. 30($d$) is an enlarged, perspective view of part of the end effector and part of the instrument of FIG. 30($a$);

FIG. 37 is a perspective view of another minimally invasive surgical instrument according to the invention;

FIGS. 41(a) to 41(e) are schematic views illustrating movement of an end effector of another minimally invasive surgical instrument according to the invention relative to a distal end of the instrument from a proximal end of the instrument;

FIGS. 47 and 48 are views similar to FIGS. 13(a) and 13(b) of another malleable tube part of a minimally invasive surgical instrument according to the invention;

FIGS. 49 and 50 are views similar to FIGS. 13(a) and 13(b) of another malleable tube part of a minimally invasive surgical instrument according to the invention;

FIGS. 51 and 52 are views similar to FIGS. 17(a) and 17(b) of another flexible cable part of another minimally invasive surgical instrument according to the invention; and FIGS. 53 and 54 are views similar to FIGS. 17(a) and 17(b) of another flexible cable part of another minimally invasive surgical instrument according to the invention.

DETAILED DESCRIPTION

In this specification, the term "malleable" is used to denote an element which is capable of being manipulated into a desired position and/or orientation, and which retains this manipulated position and/or orientation under the typical stresses and strains applied when used for an intended purpose with a patient, for example during partial insertion of a laparoscopic instrument through a laparoscopic cannula.

In this specification, the term "flexible" is used to denote an element which is capable of being manipulated into a desired position and/or orientation, but which does not retain this manipulated position and/or orientation without the assistance of a separate means, such as a surgeon's hand, to hold the flexible element in the manipulated position and/or orientation.

Figure 1:
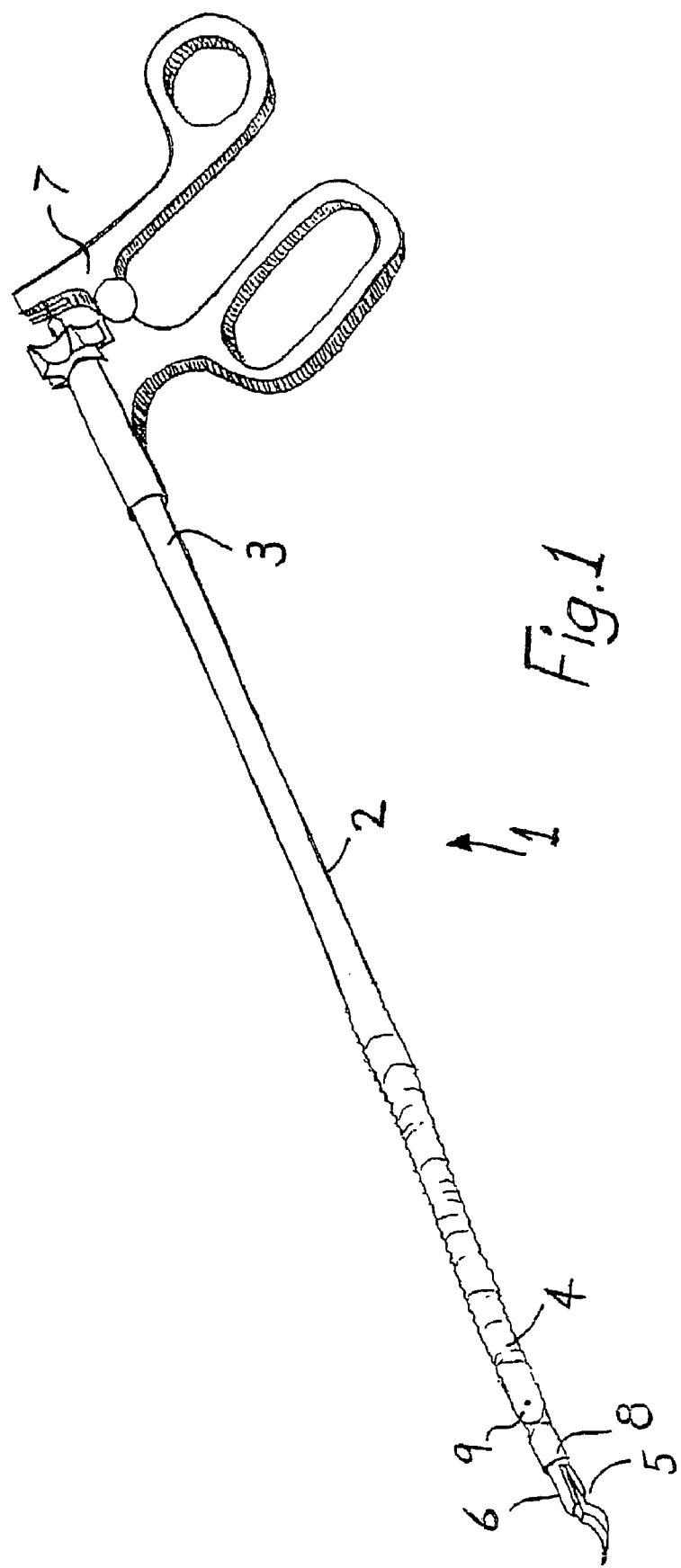
FIG. 1 is a perspective view of a minimally invasive surgical instrument according to the invention.
Figure 2:
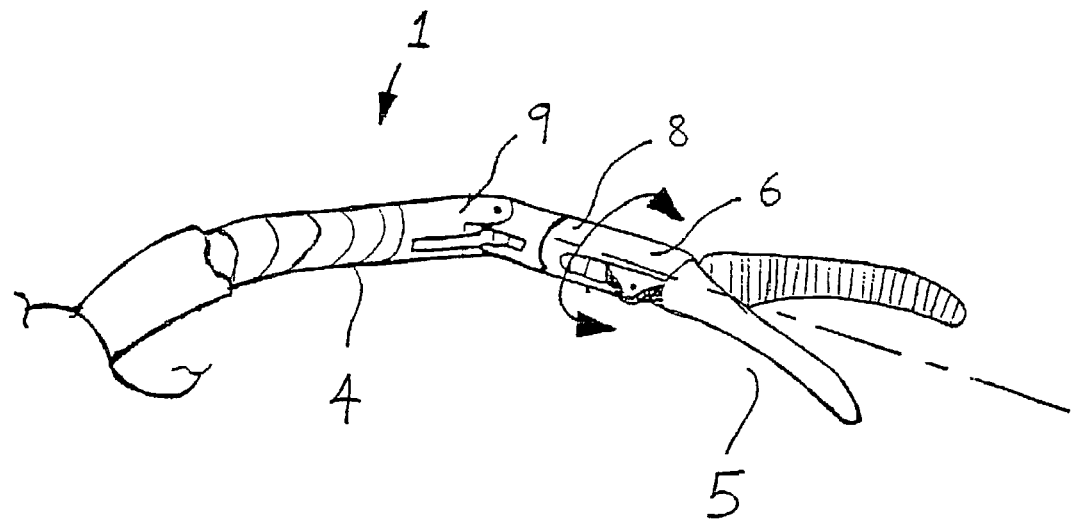
FIGS. 2 and 3 are enlarged views of part of the instrument of FIG. 1 in different positions of use.
Figure 3:
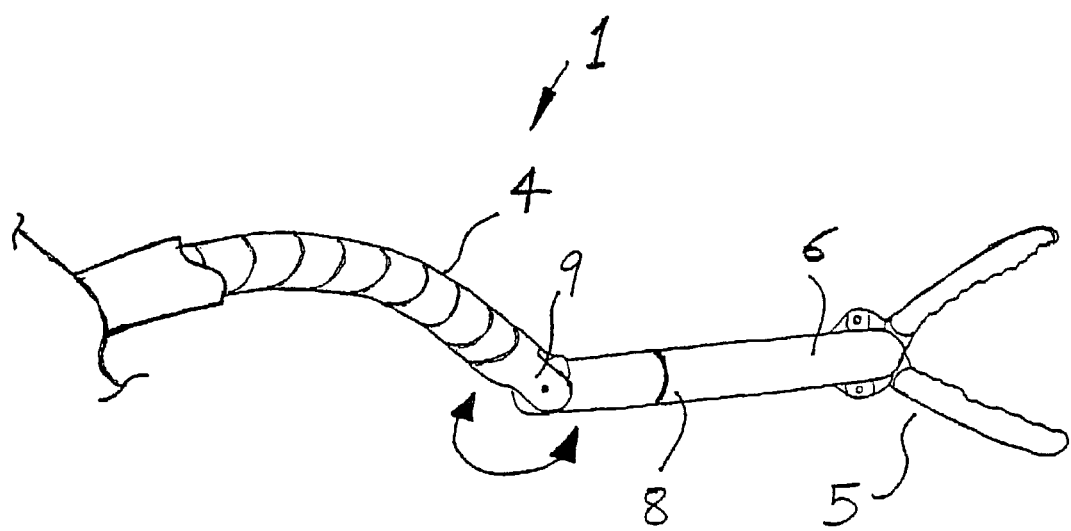

Referring to the drawings, and initially to FIGS. 1 to 3 thereof, there is illustrated a minimally invasive surgical instrument 1 according to the invention.

The minimally invasive surgical instrument 1 according to the invention is particularly suitable for use with a small opening to an operating space, such as a trocar puncture opening as typically used during laparoscopic surgery. The radial dimension of the working channel provided through a laparoscopic cannula is typically in the range of from 2 mm to 15 mm.

An example of use of the surgical instrument of the invention is to carry out a procedure in an abdominal cavity during a minimally invasive abdominal surgical procedure.

The instrument 1 comprises an elongate stem 2 extending between a proximal end 3, which in use is located externally of an operating space, and a distal end 4, which in use is inserted into the operating space.

The instrument 1 has an end effector 5, at the distal end 4 of the stem 2, and an actuating handle 7 at the proximal end 3 of the stem 2. The end effector 5 comprises a proximal main body 6 and distal operating means, such as grasping fingers or cutting fingers.

At least portion of the stem 2 is malleable. This facilitates insertion of the distal end 4 of the stem 2 into an operating space in a low-profile, substantially straightened configuration, and subsequent manipulation of the distal end 4 of the stem 2, for example by a surgeon's hand, into a desired position and/or orientation within the operating space. The malleable stem 2 maintains this manipulated position and/or orientation within the operating space.

As illustrated in FIGS. 2 and 3, the end effector main body 6 is mounted to the distal end 4 of the stem 2. At least one, and in this case two, joints 8, 9 are provided in the region of mounting of the end effector 5 to the distal end 4 of the stem 2. One joint 8 facilitates an independent rotational movement of the end effector main body 6 about a longitudinal axis running through the end effector 5 relative to the distal end 4 of the stem 2 (FIG. 2). The other joint 9 facilitates an independent pivoting movement of the end effector main body 6 relative to the distal end 4 of the stem 2 (FIG. 3). In this case the pivoting joint 9 is a hinge joint, and the rotational joint 8 is distal of the pivoting joint 9, as illustrated.

Referring now to FIGS. 4 to 8, use of the minimally invasive surgical instrument 1 according to the invention to perform a minimally invasive surgical procedure is illustrated.

A cannula 10 is partially inserted through an opening 11 to an operating space 12, and the instrument 1 is then partially inserted through the cannula 10 so that the proximal end 3 of the stem 2 is located externally of the operating space 12 and the distal end 4 of the stem 2, with the end effector 5 mounted thereto, is located within the operating space 12 (FIG. 4).

The stem 2 is manipulated, for example by a surgeon's gloved hand 13, into a desired position and/or orientation within the operating space 12 (FIG. 5). The malleable nature of the stem 2 maintains the distal end 4 of the stem 2 in the desired manipulated position and/or orientation with the operating space 12, even after the stem 2 has been released by the surgeon's hand 13 (FIG. 6).

When the distal end 4 of the stem 2 is in a desired position and/or orientation within the operating space 12, the end effector main body 6 can be moved, for example rotated about joint 8, in an independent manner relative to the distal end 4 of the shaft 2 (FIG. 7) for carrying out a desired surgical procedure in the operating space 12, for example cutting away a piece of diseased tissue.

Figure 7:
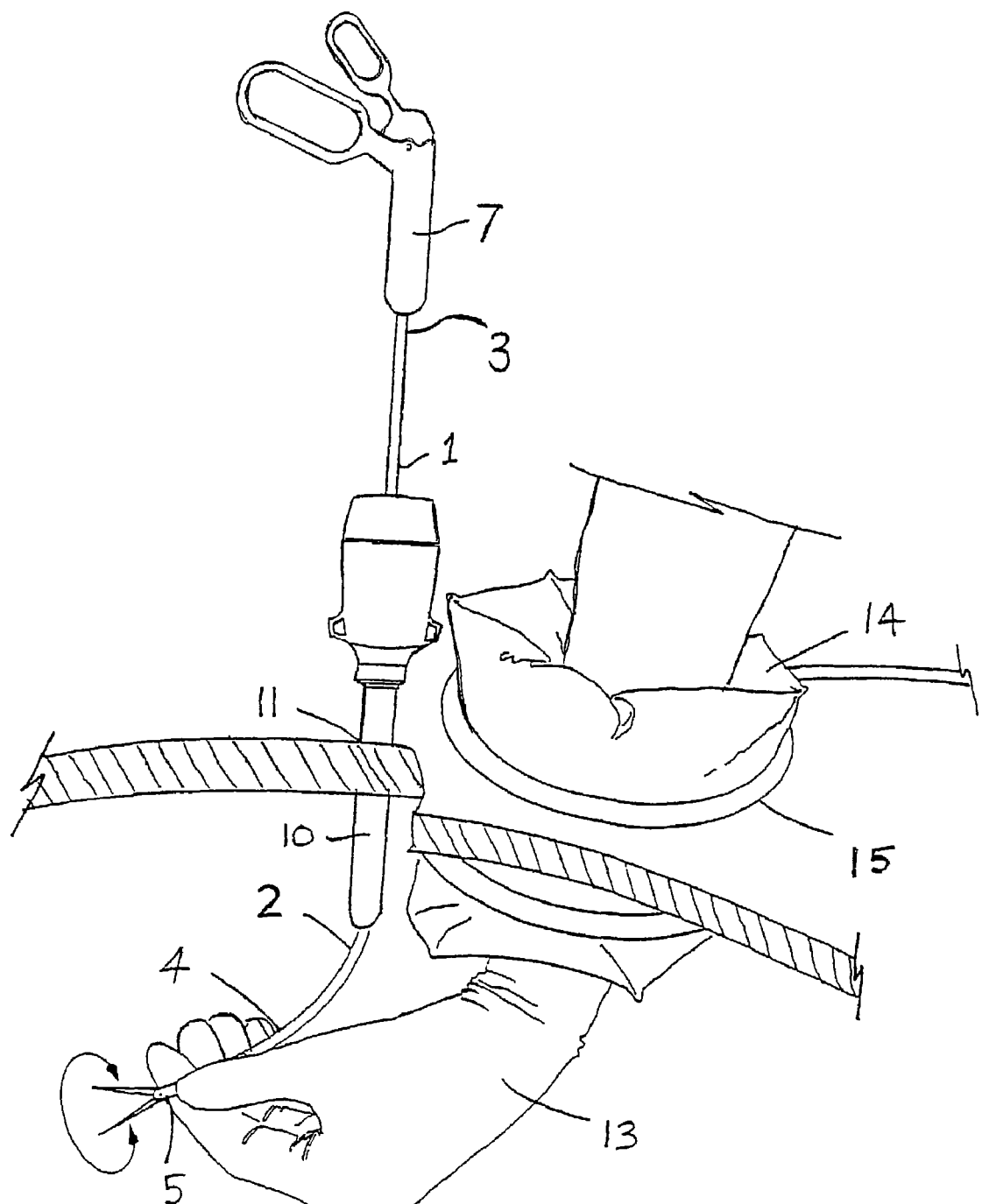
FIGS. 7 and 8 are schematic views illustrating movement of an end effector of the instrument of FIG. 6 relative to a distal end of the instrument.
Figure 8:
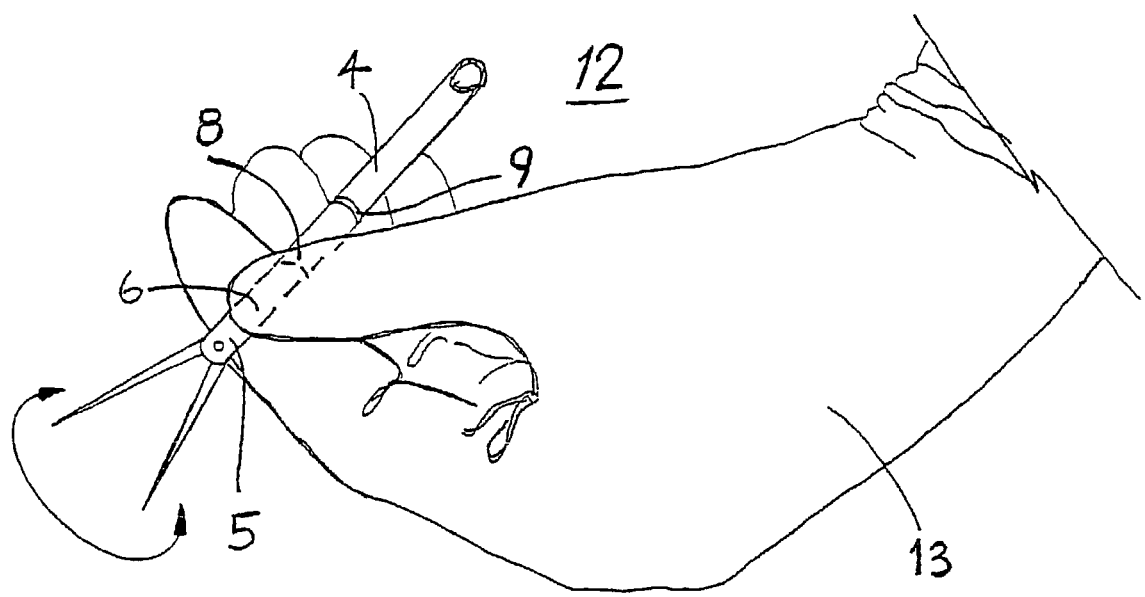

In this case, the end effector main body 6 is rotated relative to the distal end 4 of the stem 2 by the surgeon's hand 13, which has been inserted into the operating space 12 through a hand-access device 14 mounted at another opening 15 to the operating space 12 (FIGS. 7 and 8).

One example of an application of the instrument 1 according to the invention is to carry out a surgical procedure in the lower pelvis. The malleable stem 2 can be manipulated into a desired position and/or orientation so that the stem 2 extends over the pelvic bone. This manipulated position and/or orientation is maintained by the design strength of the stem 2. The end effector main body 6 can then be moved independently of the distal end 4 of the stem 2 to approach the gall bladder with the end effector 5, as desired. The enhanced degrees of freedom provided by the joints 8, 9 at the distal end 4 of the malleable stem 2 enables the surgeon to carry out potentially difficult or awkward surgical procedures quickly and easily.

The end effector main body 6 may have a knurled or ridged outer surface to provide tactile indication to the surgeon of the orientation of the end effector 5 relative to the distal end 4 of the stem 2.

Figure 9:
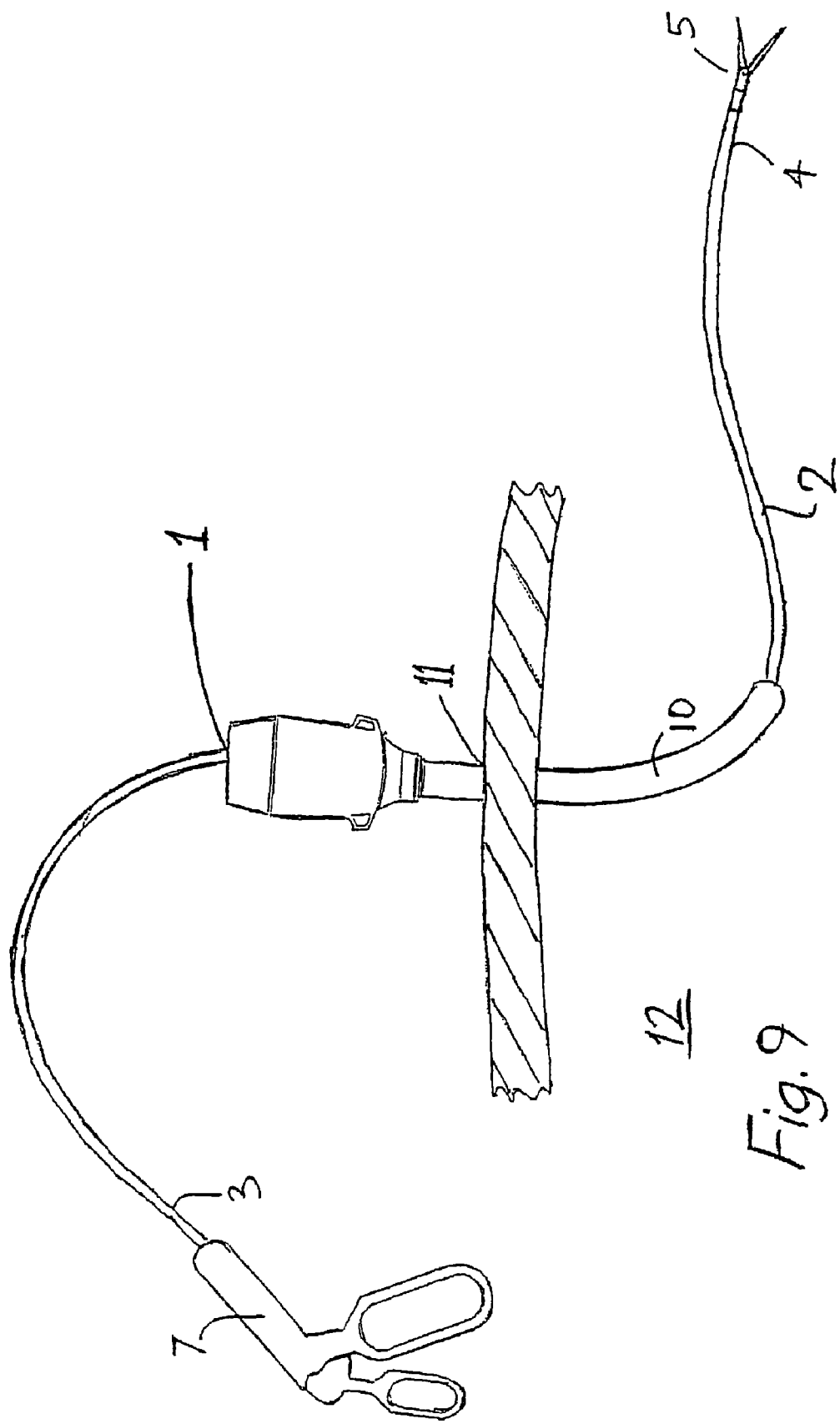
FIG. 9 is a schematic view of the instrument of FIG. 5 after another manipulation.

The surgical instrument 1 of the invention is particularly suitable for use with an at least partially flexible cannula, preferably a distally flexible cannula 10. The flexible cannula 10 enables the malleable instrument 1 to be inserted and moved through the cannula 10 in a desired manipulated position and/or orientation. Manipulation of the distal end 4 of the stem 2 into a desired position and/or orientation in the operating space 12 may bend or manipulate such a flexible cannula 10, as illustrated in FIG. 9.

The cannula 10 may also be directly manipulated by the surgeon's intra-pneumoperitoneal hand 13, and/or by another surgical instrument.

The stem 2 of the surgical instrument 1 is shown in more detail in FIGS. 10 to 28. The stem 2 comprises an outer shaft 20 and an inner elongate member 23.

The outer shaft 20 comprises a proximal rigid tube 21 and a distal malleable tube 22 (FIGS. 10 to 13). The malleable tube 22 comprises an inner spring coil 22a, an intermediate spring coil 22b with a greater pitch than the inner spring coil 22a, and an outer shrink-wrapped tube 22c (FIGS. 13(a) and 13(b)).

The outer tube 22c acts as a gas-tight sealing jacket around the spring coils 22a, 22b. This sealing effect is particularly important when the instrument 1 is used during laparoscopy to prevent insufflation gas from escaping through the malleable tube 22. In this manner, pneumoperitoneum within the operating space 12 is maintained even during manipulation of the stem 2.

Figure 13D:
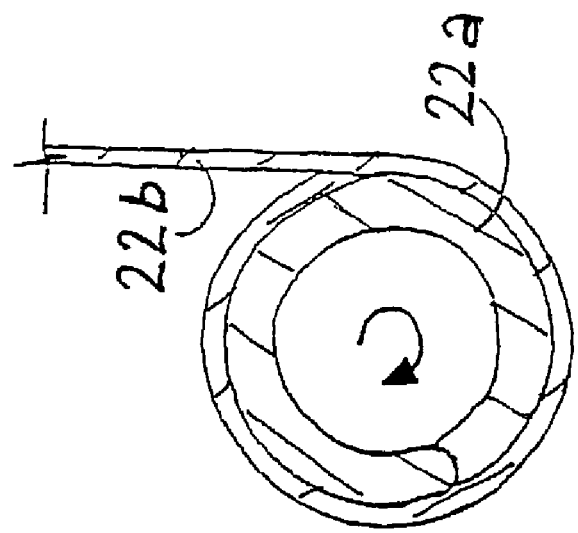
FIG. 13 is a perspective view of the tube of FIG. 11.
Figure 13C:
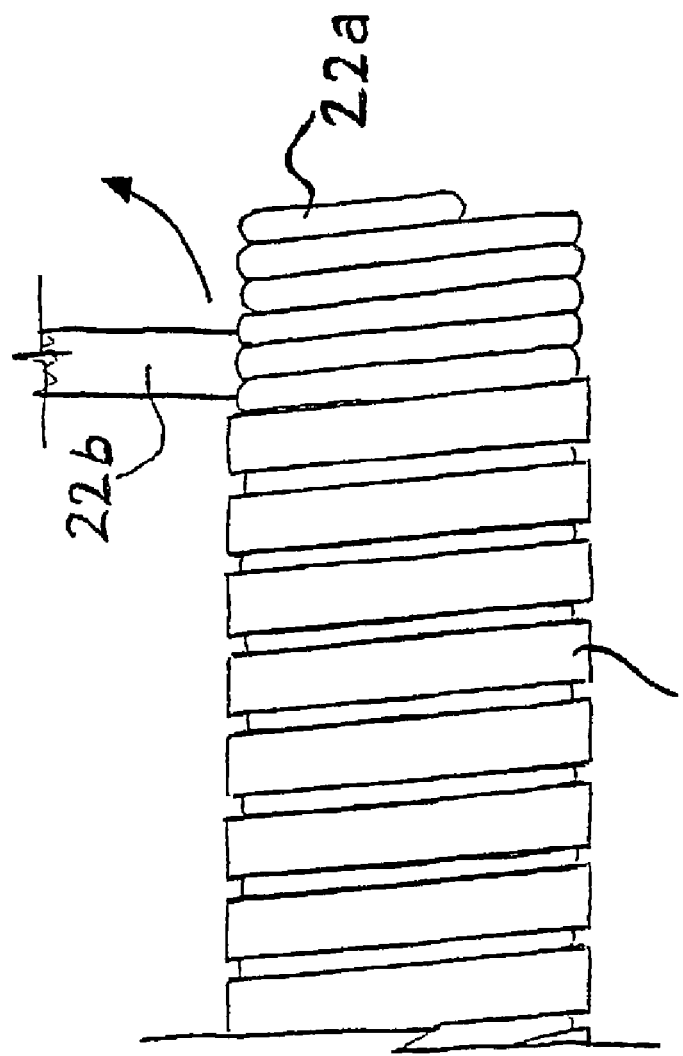

To form the tube 22, the intermediate spring coil 22b is wrapped around the inner spring coil 22a (FIGS. 13(c) and 13(d)), and the outer tube 22c is shrink-wrapped around the spring coils 22a, 22b.

The inner elongate member 23 comprises a proximal rigid rod 24 and a distal flexible cable 25 (FIGS. 14 to 17).

The flexible cable 25 comprises a braid of inner wires 25a and an outer wire coil 25b (FIGS. 17(a) and 17(b)). To form the cable 25, the outer wire coil 25b is wrapped around the braid of inner wires 25a (FIGS. 17(a) and 17(b)).

The inner elongate member 23 is assembled by inserting a distal end 26 of rod 24 into a proximal end 27 of a first coupling tube 28, and inserting a proximal end 29 of cable 25 into a distal end 30 of the coupling tube 28. The rod 24, the cable 25 and the coupling tube 28 are then silver soldered together to secure the assembly. A distal end 31 of cable 25 is then inserted into a proximal end 32 of a second coupling tube 33, and the coupling tube 33 is silver soldered to the cable 25 to form the inner elongate member 23, as illustrated in FIGS. 22 and 23.

Figure 24A:
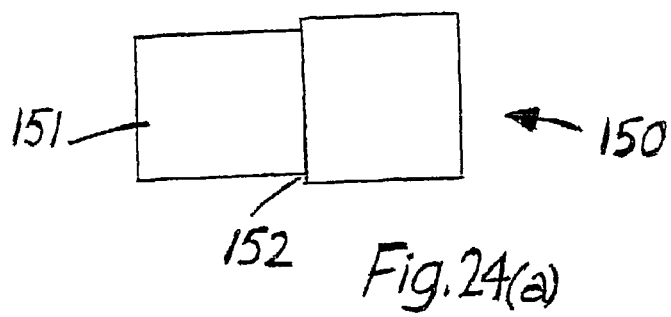
FIG. 24($a$) is a side view of a spacer element part of the instrument of FIGS. 1 to 9.
Figure 24C:
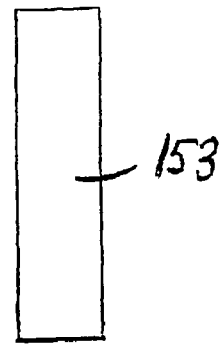
Figure 24B:
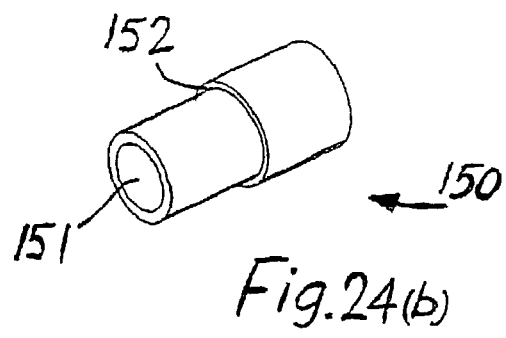
Figure 24D:
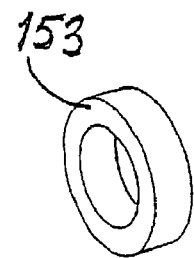
Figure 24E:
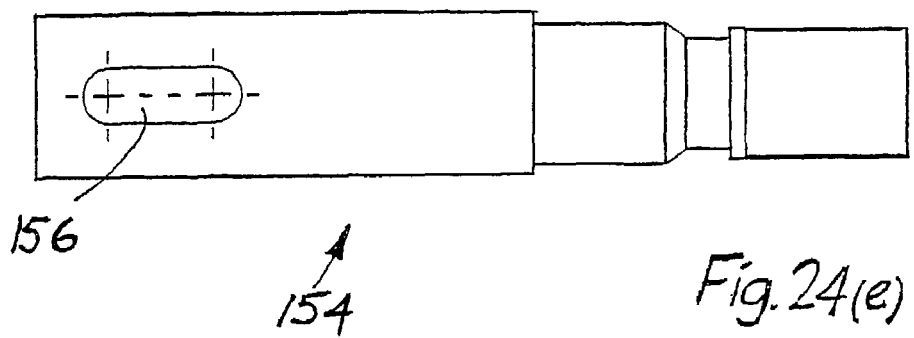
Figure 24F:
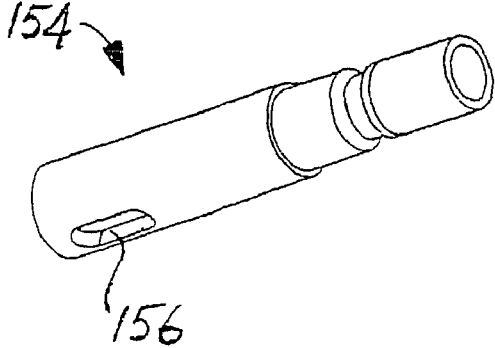

The outer shaft 20 is assembled by overlapping a proximal end 34 of the malleable tube 22 over a distal end 35 of the rigid tube 21. A proximal end 151 of a spacer element 150, as illustrated in FIGS. 24(a) and 24(b), is inserted into a distal end 36 of the malleable tube 22 until a shoulder 152 on the spacer 150 engages the tube 22. A spring washer 153 is aligned distally of the spacer 150, and an end effector connector piece 154 is aligned distally of the washer 153. The spring washer 153 and the end effector connector piece 154 are illustrated in FIGS. 24(c) to 24(f). The assembled inner elongate member 23 is then inserted through the assembled outer shaft 20, as illustrated in FIGS. 25 and 26, to form the stem 2 of the surgical instrument 1. A fixing pin 155 is inserted through co-operating apertures 156, 157 in the end effector connector piece 154 and the second coupling tube 33 respectively, to secure the stem assembly, as illustrated in detail in FIG. 27.

Figure 28:
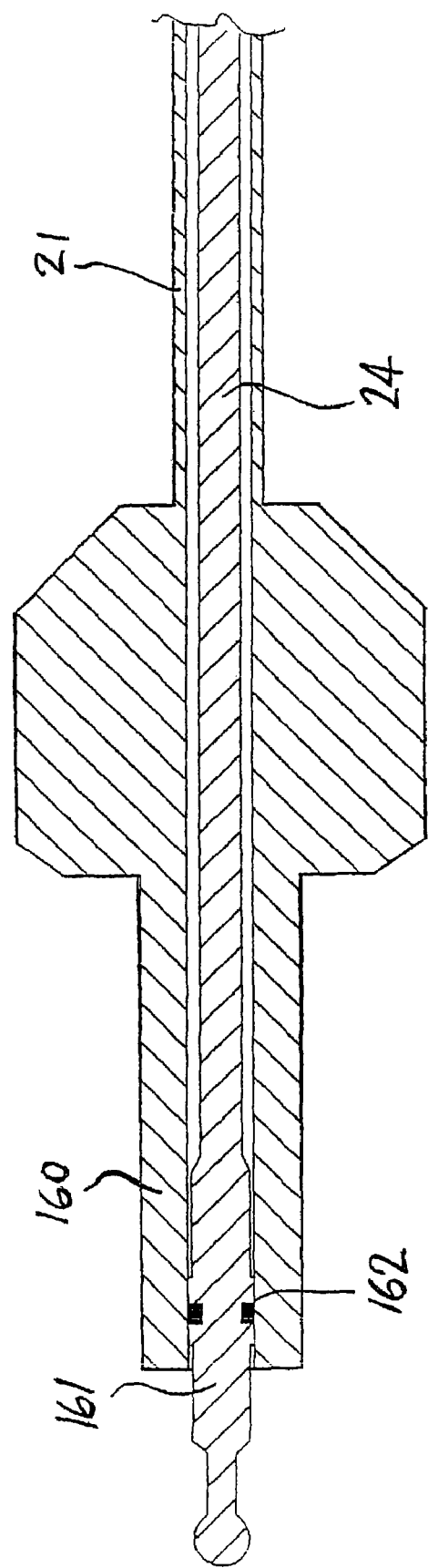
FIG. 28 is an enlarged, side view of another part of the assembly of FIGS. 25 and 26.
Figure 30A:
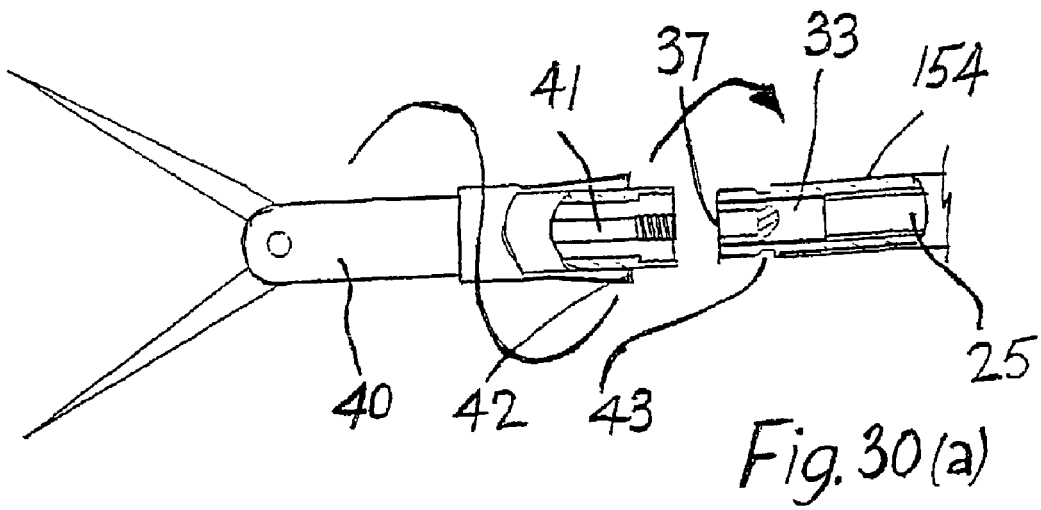
FIGS. 30($a$) to 30($c$) are side, partially cross-sectional views illustrating mounting of an end effector to a distal end of another minimally invasive surgical instrument according to the invention.
Figure 30B:
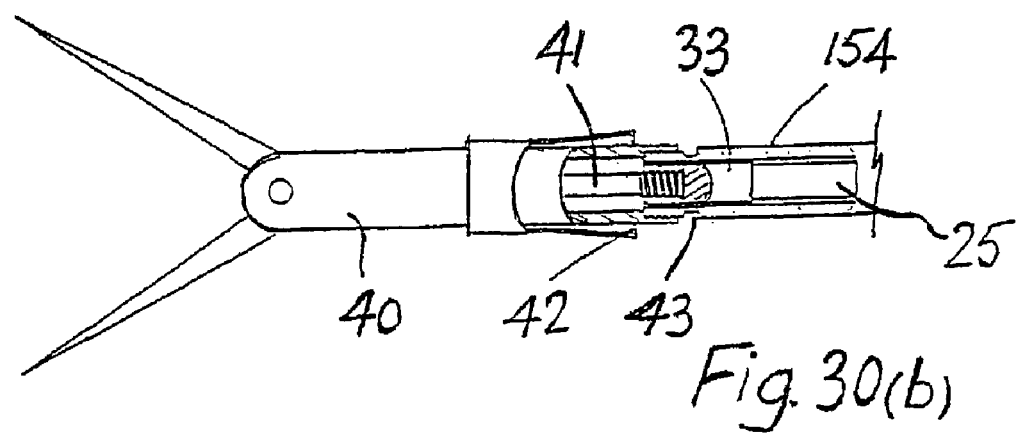
Figure 30C:
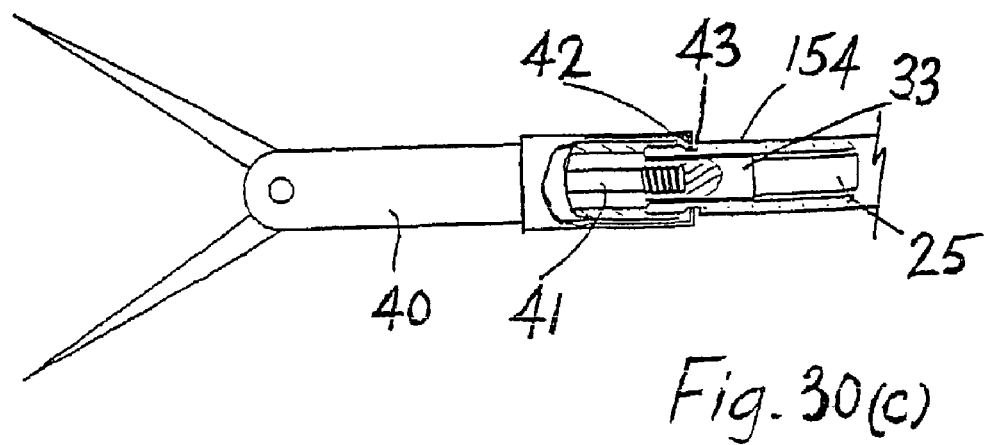
Figure 30D:
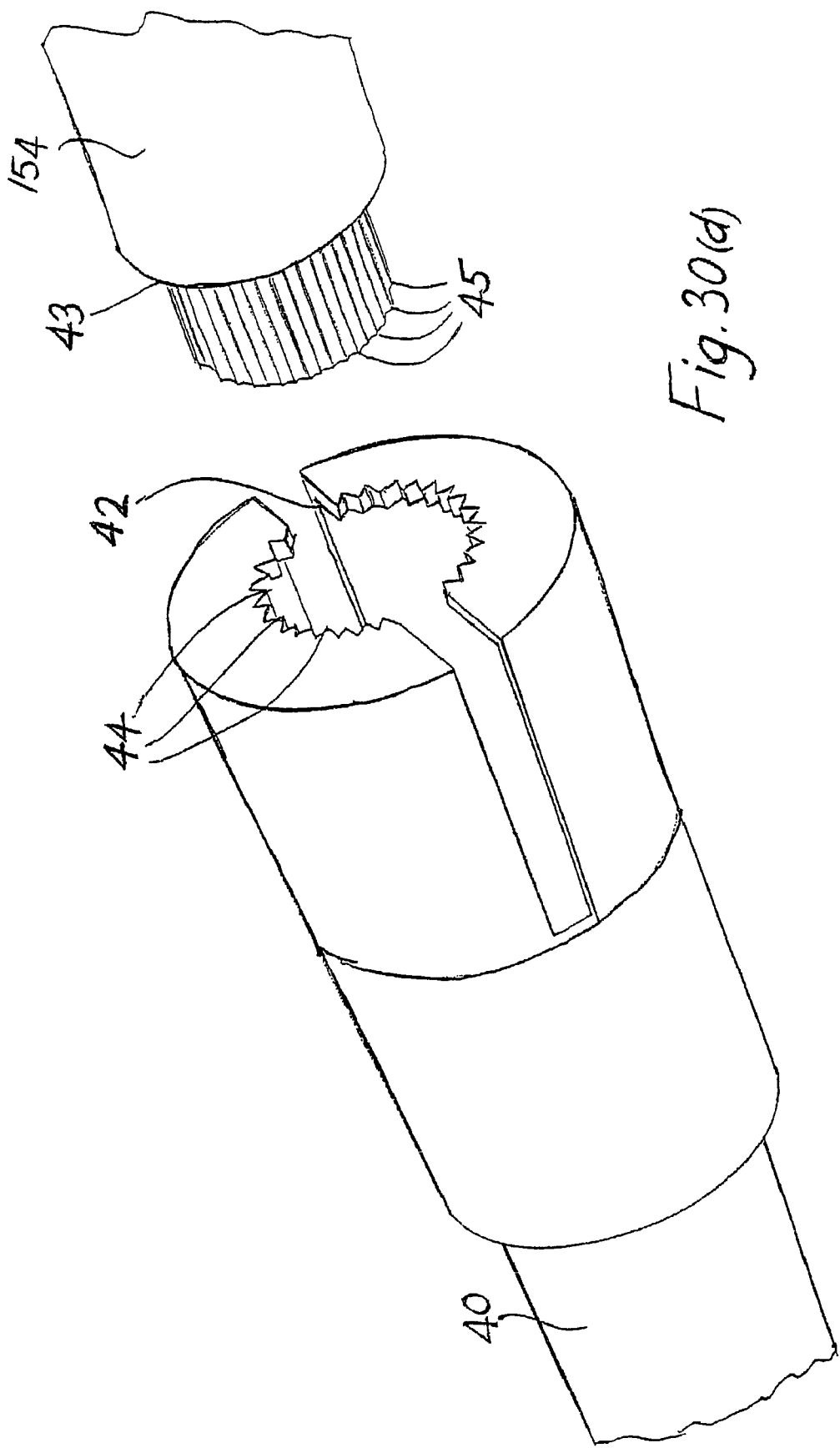

An internal O-ring lip seal 162 is provided between a proximal end 161 of the rod 24 and a proximal end 160 of the rigid tube 21, as illustrated in FIG. 28. The O-ring seal 162 is particularly important when the instrument 1 is used during laparoscopy, to prevent insufflation gas from escaping through the space between the outer shaft 20 and the inner elongate member 23. In this manner, pneumoperitoneum within the operating space is maintained even during movement of the inner elongate member 23 relative to the outer shaft 20.

FIGS. 29(a) to 29(d) illustrate mounting of the end effector 5 to the stem 2. The end effector 5 is threadably mounted in a releasable manner to the distal end 4 of the stem 2 by screwing the end effector 5 to the end effector connector piece 154 engaging thread formations on the end effector 5 with corresponding thread formations on the end effector connector piece 154 engaging thread formations on the end effector 5 with corresponding thread formations on the end effector connector piece 154, as illustrated in FIGS. 29(a) to 29(d). A distal end 37 of the coupling tube 33 also has thread formations which threadingly engage with corresponding thread formations on inner tongue 41 in the end effector 5 in a releasable manner during screwing of the end effector 5 to the end effector connector piece 154 (FIGS. 29(a) to 29(d)).

It will be appreciated that the instrument 1 may additionally or alternatively be manipulated externally of the operating space 12 before inserting the instrument 1 partially through the flexible cannula 10 into the operating space 12.

It will further be appreciated that the instrument 1 may additionally or alternatively be manipulated during the partial insertion of the instrument 1 through the cannula 10 by levering the proximal end 3 of the stem 2 about the cannula 10 in the opening 11 when the instrument 1 is partially inserted through the cannula 10.

These procedures may aid the surgeon in accessing regions in the operating space 12 which are laterally remote of the opening 11. In addition the surgeon can adapt to the physiological characteristics of the patient, for example the thickness of the abdomen wall, or the strength of the abdomen muscle.

It will be appreciated that the stem 2 may be malleable along the entire length of the stem 2 provided that the distal end 4 of the stem 2 can be manipulated into and maintained in a desired position and/or orientation in the operating space 12.

It will further be appreciated that the malleability of the malleable portion of the stem 2 may vary along the length of the malleable portion of the stem 2.

Further it will be appreciated that the malleability of the malleable portion of the stem 2 may be adjusted while the instrument 1 is at least partially inserted through the cannula 10 into the operating space 12. This may be achieved by, for example, an adjustment mechanism externally of the operating space 12, such as by two separate wires to adjust the malleability of the stem 2.

A proximal portion of the stem 2 adjacent a proximal end 3 of the stem 2 may be flexible. This flexible proximal portion enables a surgeon to hold the actuating handle 7, which is jointed to the proximal end 3 of the stem 2, in any suitable or comfortable position during use. This may provide for a more ergonomic surgical instrument.

FIGS. 30(a) to 30(d) illustrate mounting of another end effector 40 to the stem 2. End effector 40 is similar to the end effector 5 of FIGS. 1 to 29, and similar elements in FIGS. 30(*a*) to 30(*d*) are assigned the same reference numerals.

In the case of end effector 40, only one joint, the rotational joint 8, is provided in the region of mounting of the main body of the end effector 40 to the distal end 4 of the stem 2 to facilitate independent rotational movement of the main body of the end effector 40 relative to the distal end 4 of the stem 2.

The end effector 40 is threadably mounted in a releasable manner to the distal end 4 of the stem 2 by screwing the end effector 40 to the end effector connector piece 154 engaging thread formations on the end effector 40 with the corresponding thread formations on the end effector connector piece 154, as illustrated in FIGS. 30(*a*) and 30(*b*). The thread formations on the coupling tube 33 threadingly engage with the corresponding thread formations on the inner tongue 41 in the end effector 40 in a releasable manner during screwing of the end effector 40 to the end effector connector piece 154 (FIGS. 30(*a*) and 30(*b*)).

The end effector 40 comprises a lip 42 for engagement in a recess 43 on the end effector connector piece 154 to selectively limit movement of the main body of the end effector 40 relative to the distal end 4 of the stem 2, and thereby prevent demounting of the main body of the end effector 40 from the distal end 4 of the stem 2. The lip 42 is slidable along the end effector 40 between a disengaged position (FIG. 30(*b*)) and a position engaged in the recess 43 (FIG. 30 (*c*)). In the engaged position of FIG. 30(*c*), rotation of the inner elongate member 23 relative to the outer shaft 20, and thereby rotation of the end effector 40 relative to the end effector connector piece 154, is limited by the longitudinal movement of the lip 42 in the recess 43. The recess 43 is preferably sized to facilitate up to 360° rotation of the main body of the end effector 40 relative to the end effector connector piece 154 without demounting the main body of the end effector 40 from the distal end 4 of the stem 2.

As illustrated in FIG. 30(*d*), the lip 42 comprises a plurality of corrugations 44 and the recess 43 comprises a plurality of corresponding corrugations 45, so that in use the corrugations 44 and 45 mate. This ensures that the rotation of the main body of the end effector 40 relative to the end effector connector piece 154 occurs in a step wise manner.

Figure 31:
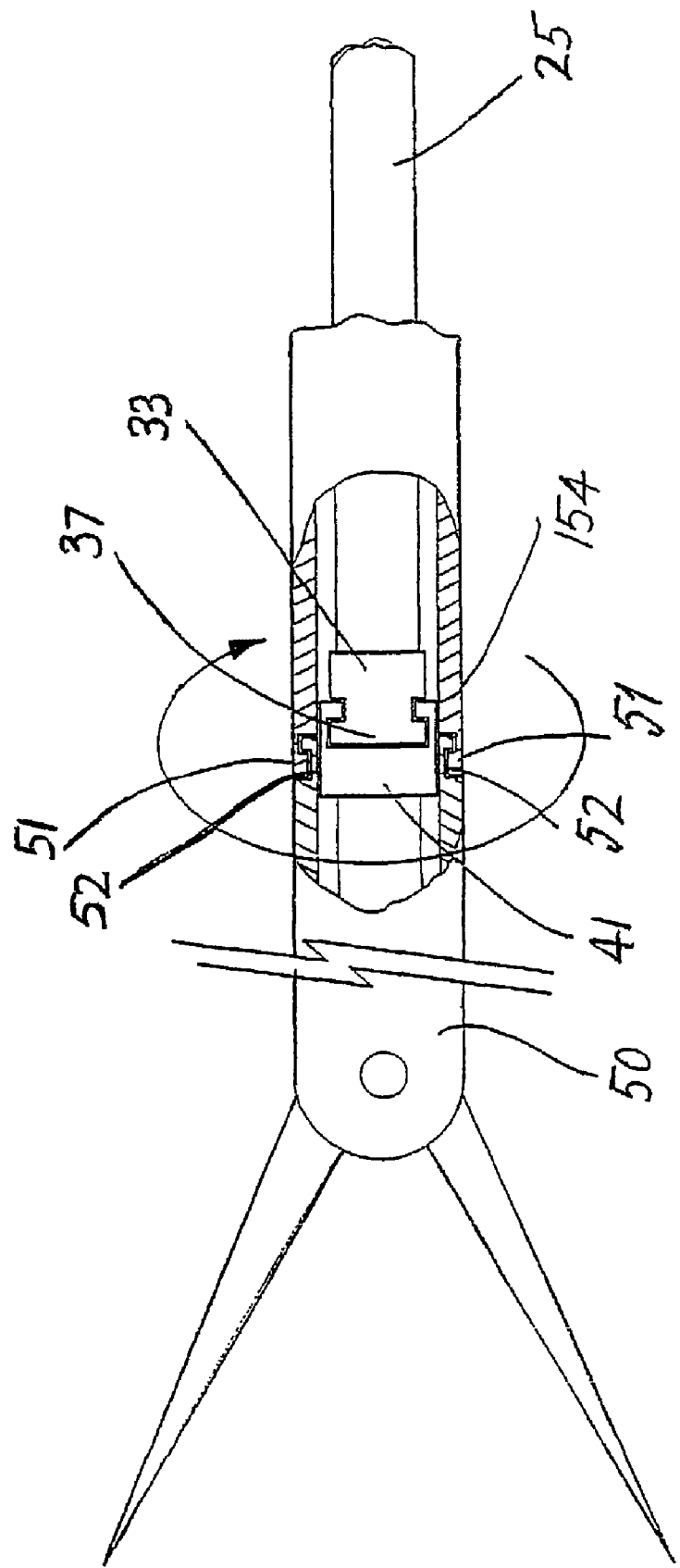
FIG. 31 is a side, partially cross-sectional view of part of another minimally invasive surgical instrument according to the invention.

Referring to FIG. 31 there is illustrated another end effector 50, which is similar to the end effector 40 of FIGS. 30(*a*) to 30(*d*), and similar elements in FIG. 31 are assigned the same reference numerals. In the case of end effector 50, only one joint, the rotational joint 8, is provided in the region of mounting of the main body of the end effector 50 to the distal end 4 of the stem 2 to facilitate independent rotational movement of the main body of the end effector 50 relative to the distal end 4 of the stem 2.

The main body of the end effector 50 is fixedly mounted to the distal end 4 of the stem 2 by means of a plurality of male projections 51 on the end effector connector piece 154 which engage in a plurality of corresponding female recesses 52 on the end effector 50. The projections 51 and recesses 52 are configured to enable rotation of the main body of the end effector 50 relative to the distal end 4 of the stem 2.

The inner tongue 41 in the end effector 50 is fixedly coupled to the distal end 37 of the coupling tube 33, as illustrated, in a manner which prevents rotation of the main body of the end effector 40 relative to the coupling tube 33.

Referring now to FIGS. 32 to 36 there is illustrated another surgical instrument 70 according to the invention, which is similar to the surgical instrument 1 of FIGS. 1 to 29, and similar elements in FIGS. 32 to 36 are assigned the same reference numerals.

Figure 32:
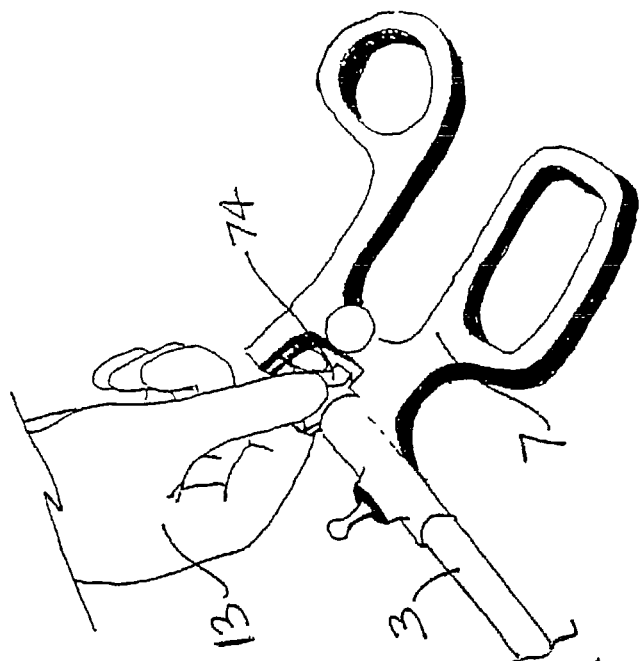
FIG. 32 is a perspective, partially cut-away view of another minimally invasive surgically instrument according to the invention.
Figure 33:
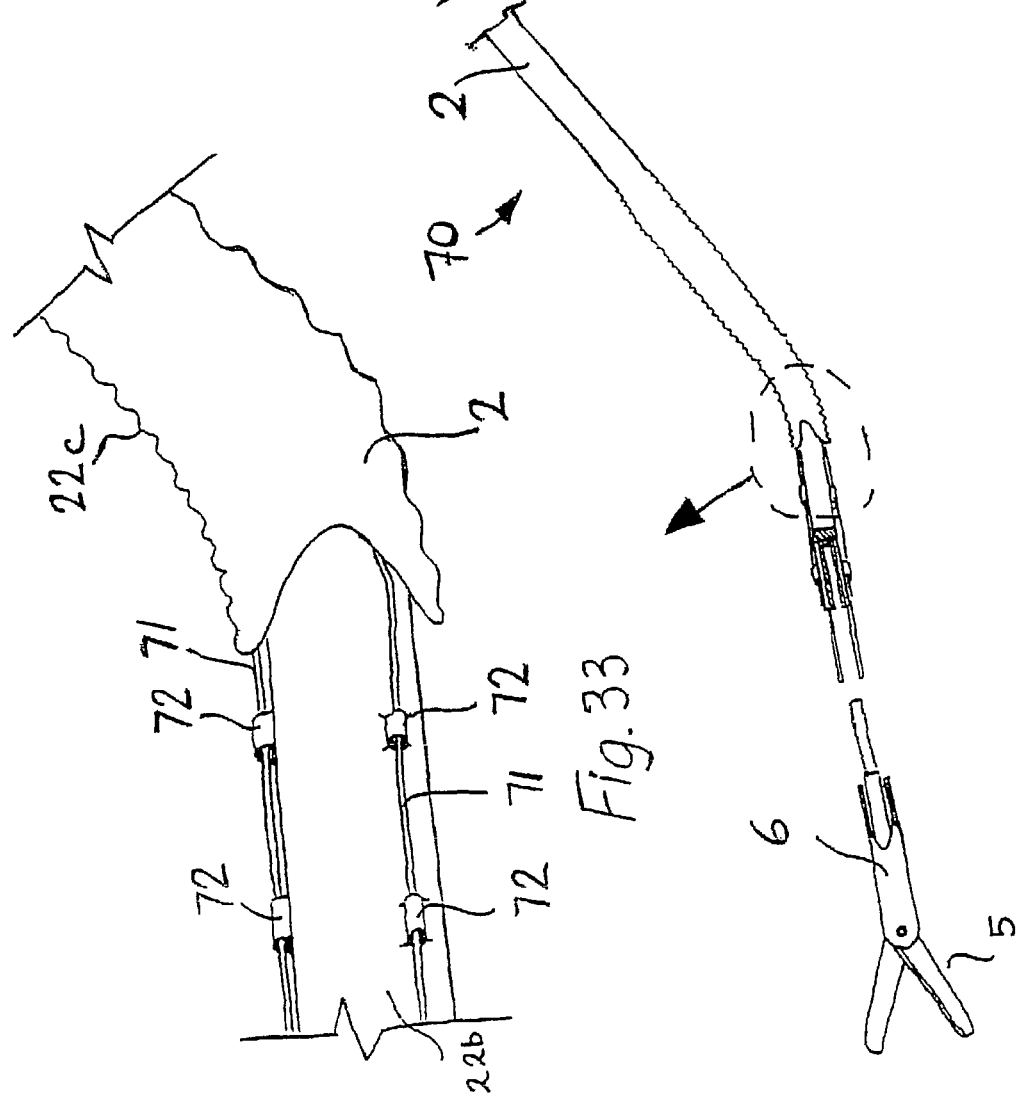
FIG. 33 is an enlarged view of part of the instrument of FIG. 32.

The instrument 70 comprises means to facilitate manipulation of the position and/or orientation of the stem 2 from the proximal end 3 of the stem 2, which in use is located externally of the operating space 12. The means is provided by at least one, and in this case four, malleable wires 71 extending along at least portion of the stem 2 (FIGS. 32 and 33). The wires 71 are slidably received in guides 72 on the stem 2, with stops at the ends of the wires 71 to limit movement of the wires 71. The wires 71 are connected proximally by a clamping arrangement to a control dial 74 on the actuating handle 7.

Figure 34:
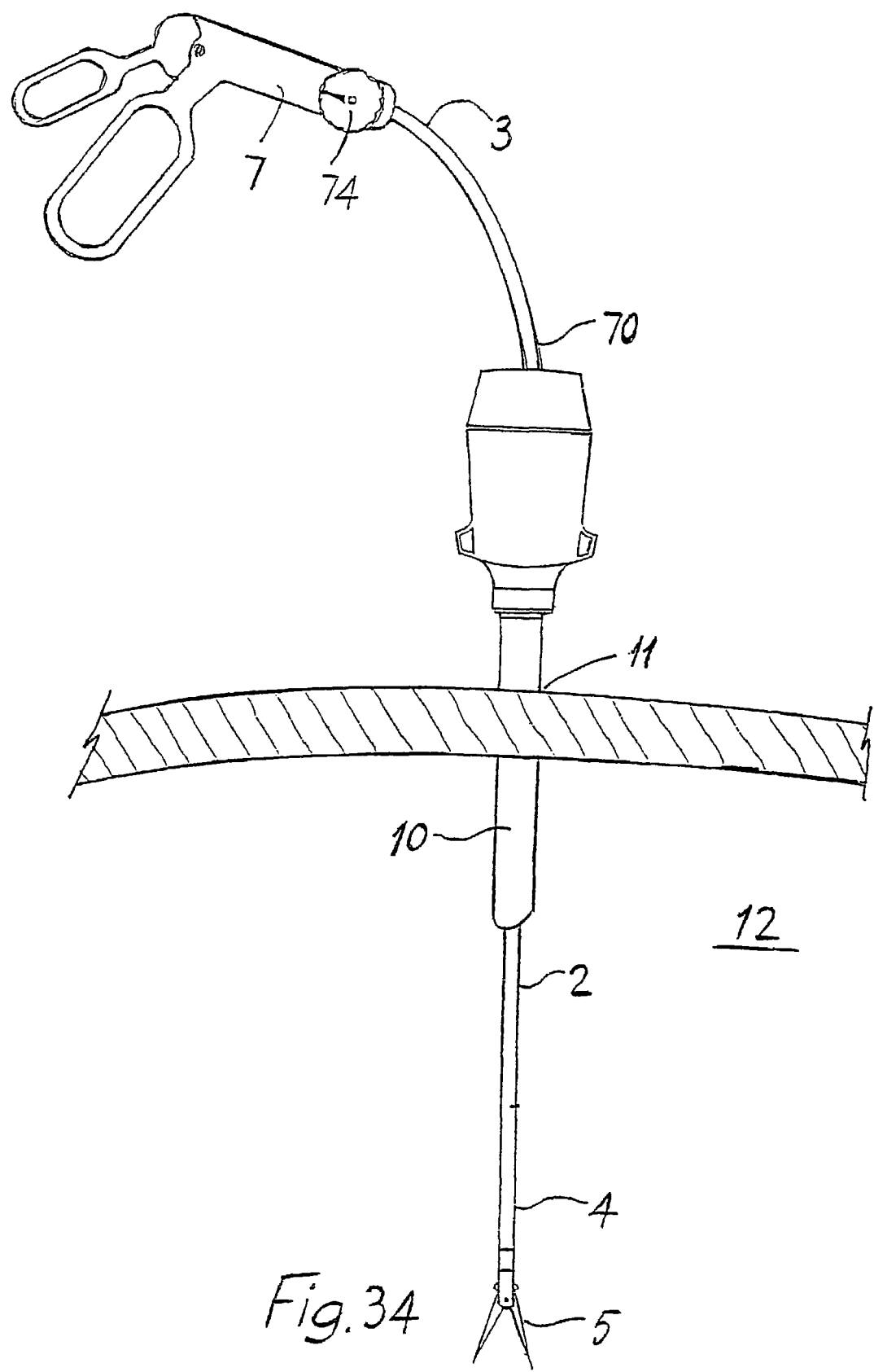
FIG. 34 is a schematic view of the instrument of FIG. 32 partially inserted through a cannula into an operating space.
Figure 35:
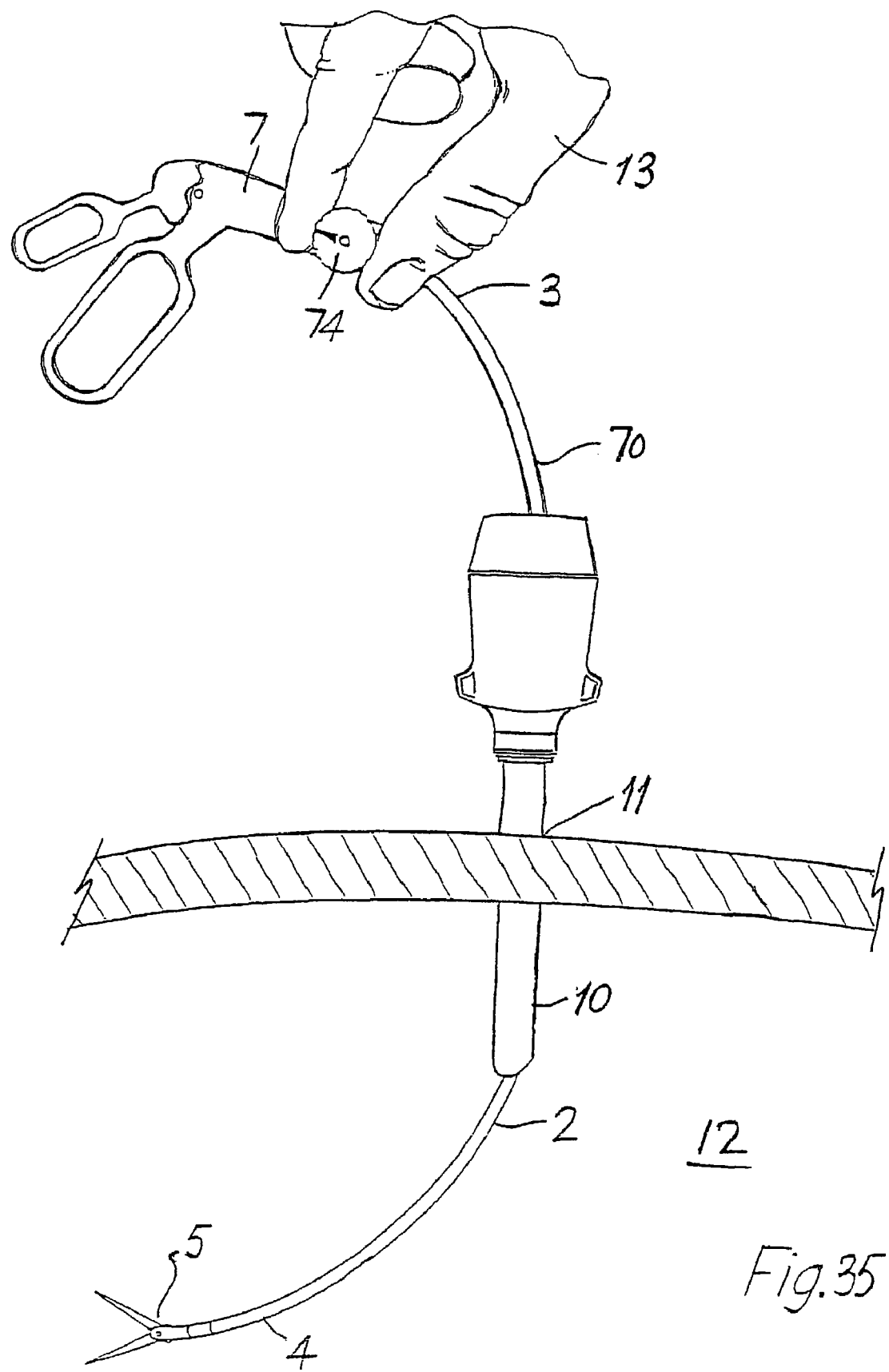
FIG. 35 is a schematic view illustrating manipulation of the instrument of FIG. 34 from externally of the operating space.

In use, the instrument 70 is partially inserted through the cannula 10 so that the end effector 5 is located within the operating space 12 (FIG. 34). The control dial 74 is then actuated by the surgeon's hand 13 externally of the operating space 12 to pull on the wires 71 and thereby manipulate the distal end 4 of the stem 2 into a desired position and/or orientation in the operating space 12 (FIG. 35).

Figure 36:
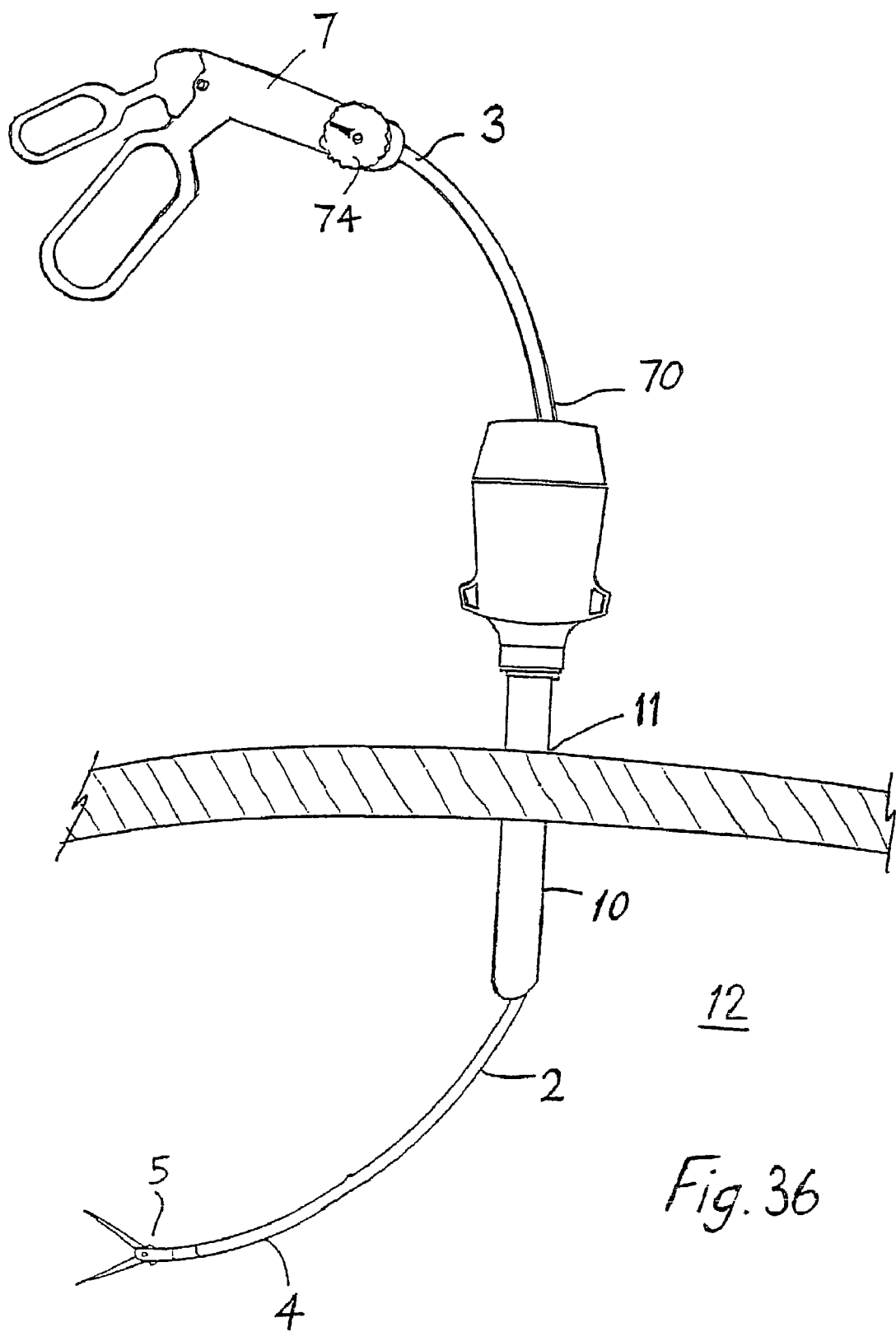
FIG. 36 is a schematic view of the instrument of FIG. 35 after manipulation.

The malleable nature of the stem 2 and the wires 71 maintains the distal end 4 of the stem 2 in the desired position and/or orientation in the operating space 12 without requiring assistance from a separate means to hold the distal end 4 of the stem 2 in the manipulated position and/or orientation (FIG. 36).

Referring to FIGS. 37 to 40, there is illustrated another surgical instrument 80 according to the invention, which is similar to the surgical instrument 70 of FIGS. 32 to 36, and similar elements in FIGS. 37 to 40 are assigned the same reference numerals.

In this case, a toggle switch 81 is provided on the actuating handle 7. The switch 81 is moveable between a position R for rotation of the main body of the end effector 5 relative to the distal end 4 of the stem 2, and a position H for pivoting or hinging movement of the main body of the end effector 5 relative to the distal end 4 of the stem 2 (FIG. 37).

Figures 38C, 38D:
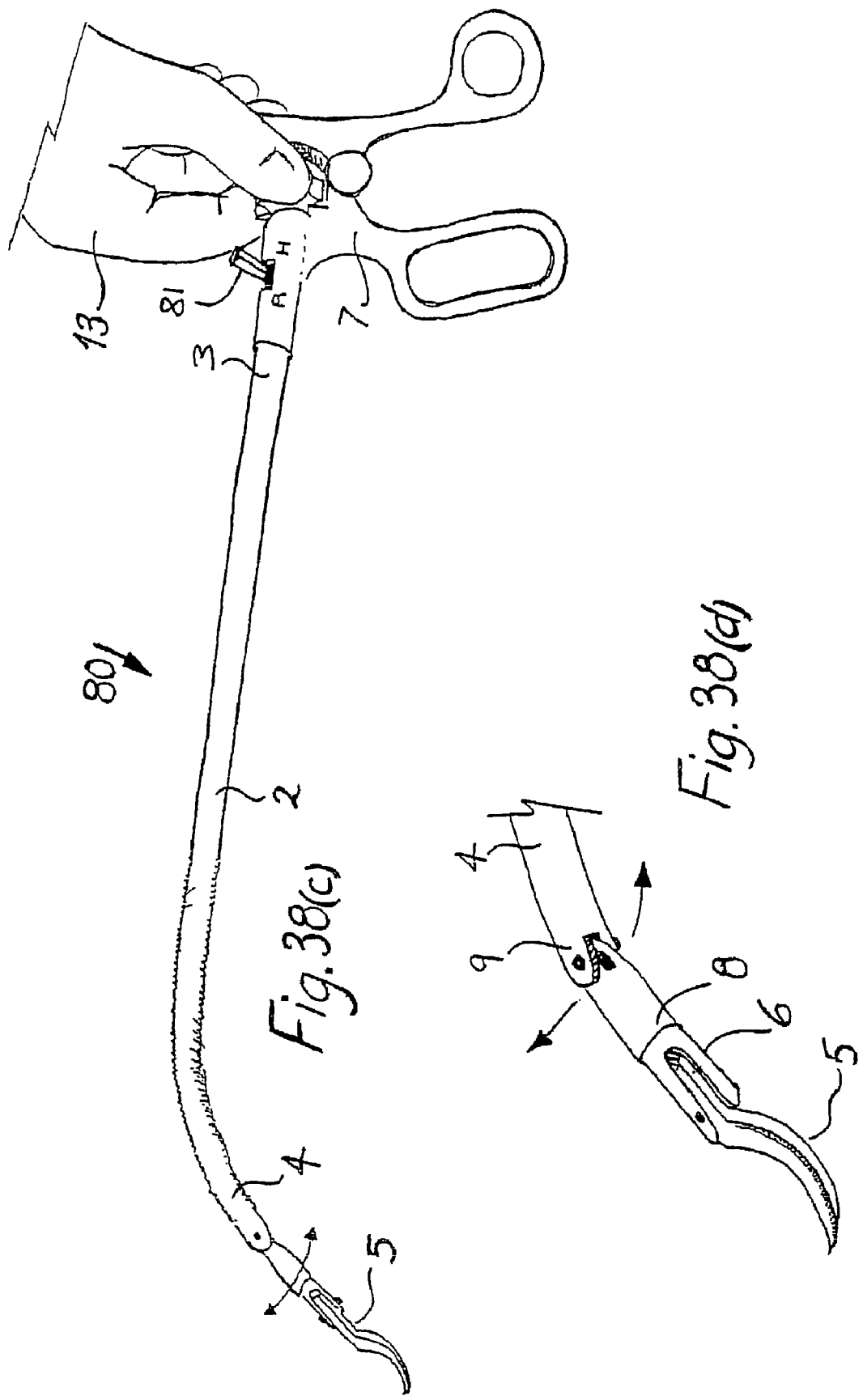
FIGS. 38($a$) to 40 are schematic views illustrating movement of an end effector of the instrument of FIG. 37 relative to a distal end of the instrument from externally of the operating space.
Figure 39:
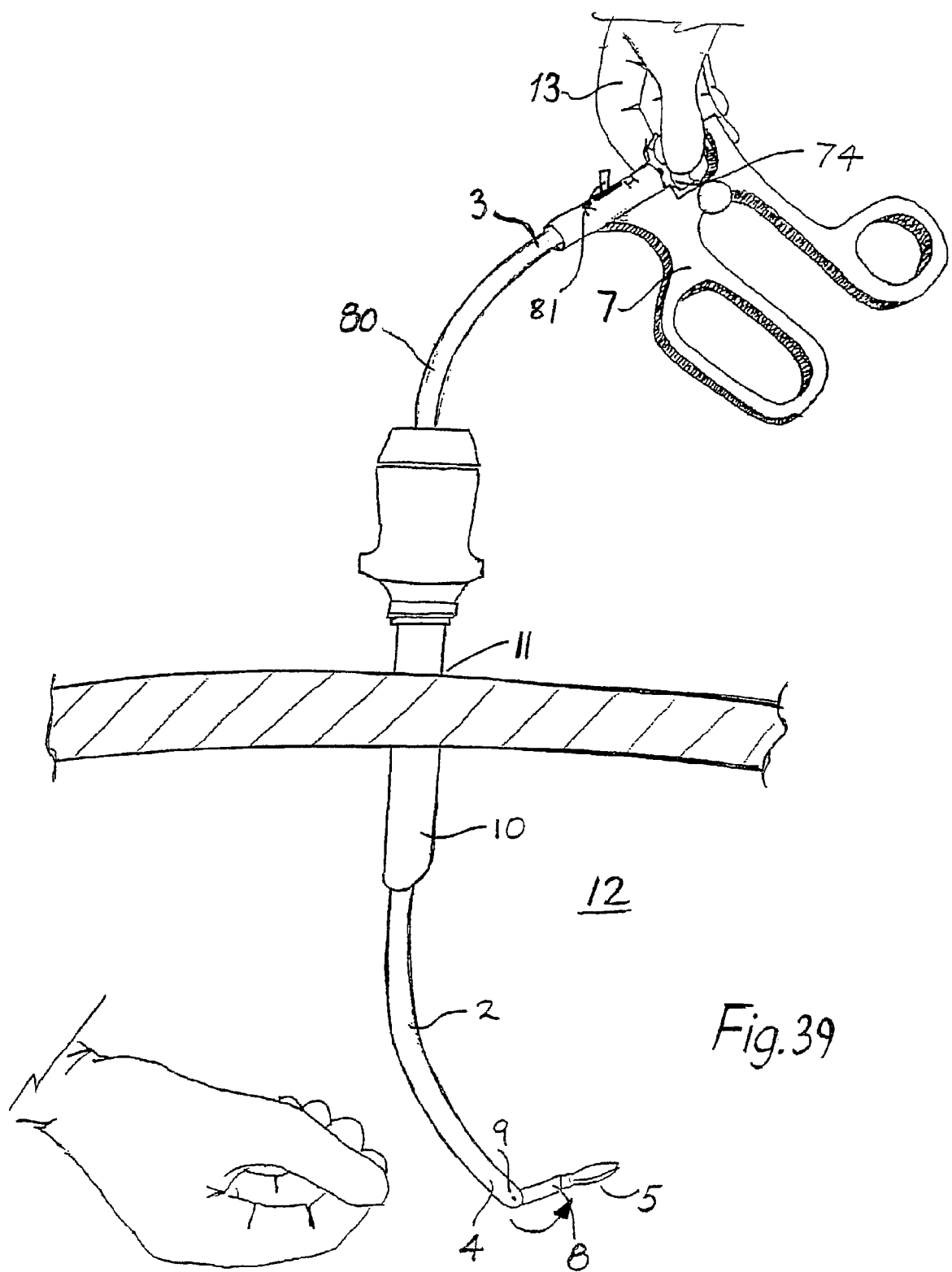
Figure 40:
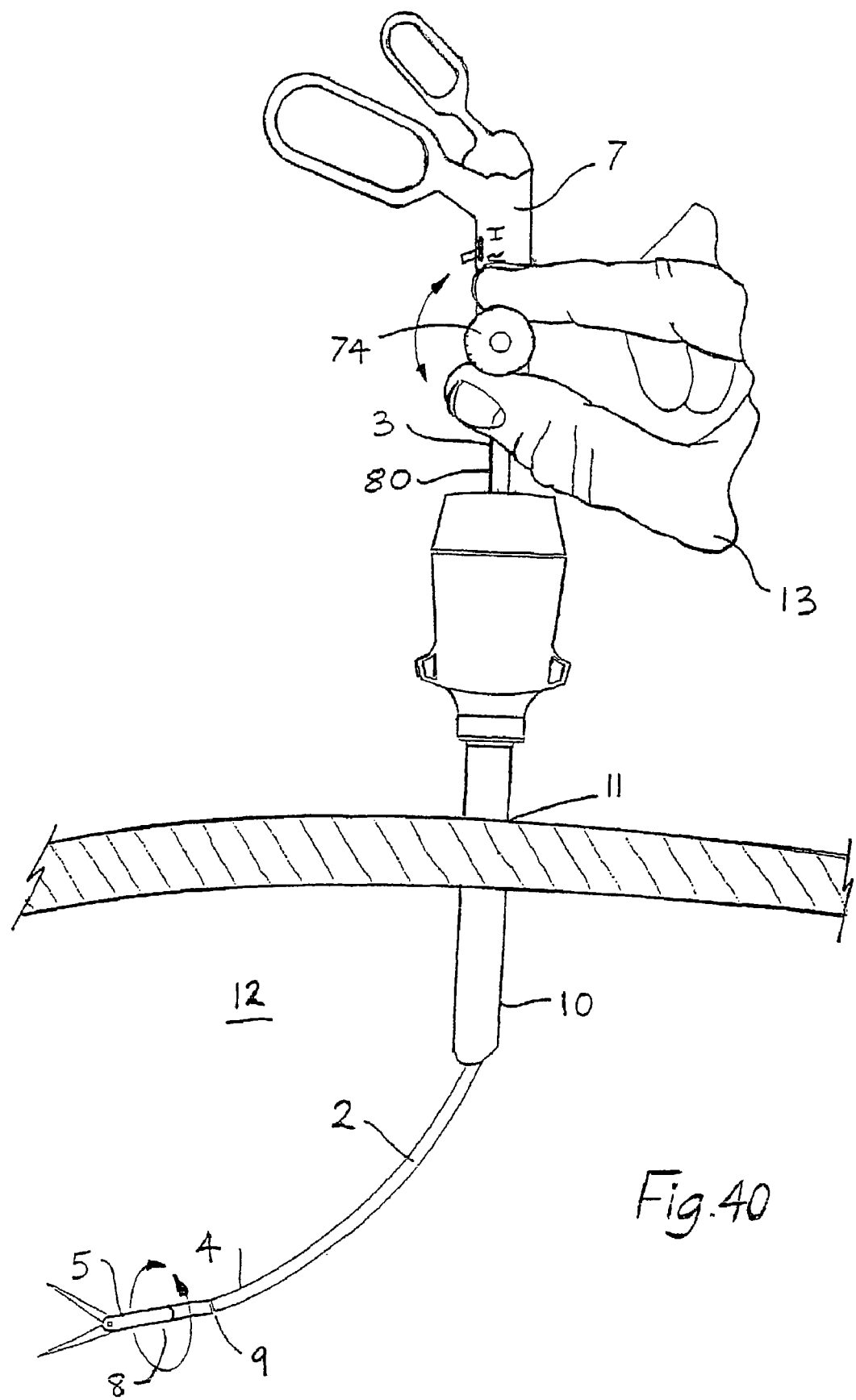

With the toggle switch 81 in position R, the control dial 74 may be actuated by the surgeon's hand 13 externally of the operating space 12 to rotate the main body of the end effector 5 relative to the distal end 4 of the stem 2 (FIGS. 38(*a*), 38(*b*) and 40). With the toggle switch 81 in position H, the control dial 74 may be actuated by the surgeon's hand 13 externally of the operating space 12 to pivot the main body of the end effector 5 relative to the distal end 4 of the stem 2 (FIGS. 38(*c*), 38(*d*) and 39).

Referring to FIGS. 41(*a*) to 41(*e*) there is illustrated another surgical instrument 60 according to the invention, which is similar to the surgical instrument 80 of FIGS. 37 to 40, and similar elements in FIGS. 41(*a*) to 41(*e*) are assigned the same reference numerals.

In this case, the pivoting joint 9 is a universal joint, the joint 9 facilitating an independent pivoting movement of the end effector main body 6 relative to the distal end 4 of the stem 2. Actuation of a joystick control 61 may be employed to pivot the end effector main body 6 relative to the distal end 4 of the stem 2 (FIG. 41(*a*)).

The rotational joint 8 facilitates an independent rotational movement of the end effector main body 6 about a longitudinal axis running through the end effector 5 relative to the distal end 4 of the stem 2. Actuation of the control dial 74 may be employed to rotate the end effector main body 6 relative to the distal end 4 of the stem 2 (FIG. 41 (*b*)).

Two malleable, lateral wires 62 extend through the stem 2 to the pivoting joint 9 to which the wires 62 are coupled for pivoting of the main body 6 of the end effector 5 relative to the distal end 4 of the stem 2 by actuation of the joystick control 61 (FIG. 41(*d*)). A malleable, central wire 63 extends through the stem 2 to the rotating joint 8 to which the wire 63 is coupled for rotation of the main body 6 of the end effector 5 relative to the distal end 4 of the stem 2 by actuation of the control dial 74 (FIG. 41 (*d*)). The central wire 63 is also operatively coupled to actuate the jaws of the end effector 5.

It will be appreciated that any desired combination of pivoting and rotating of the end effector main body 6 relative to the distal end 4 of the stem 2 may be achieved with the surgical instrument 60 by any suitable actuation of the joystick control 61 and/or the control dial 74 (FIG. 41(*e*)).

It will further be appreciated that a ball-and-socket joint may alternatively be used for the pivoting joint 9.

Figure 42:
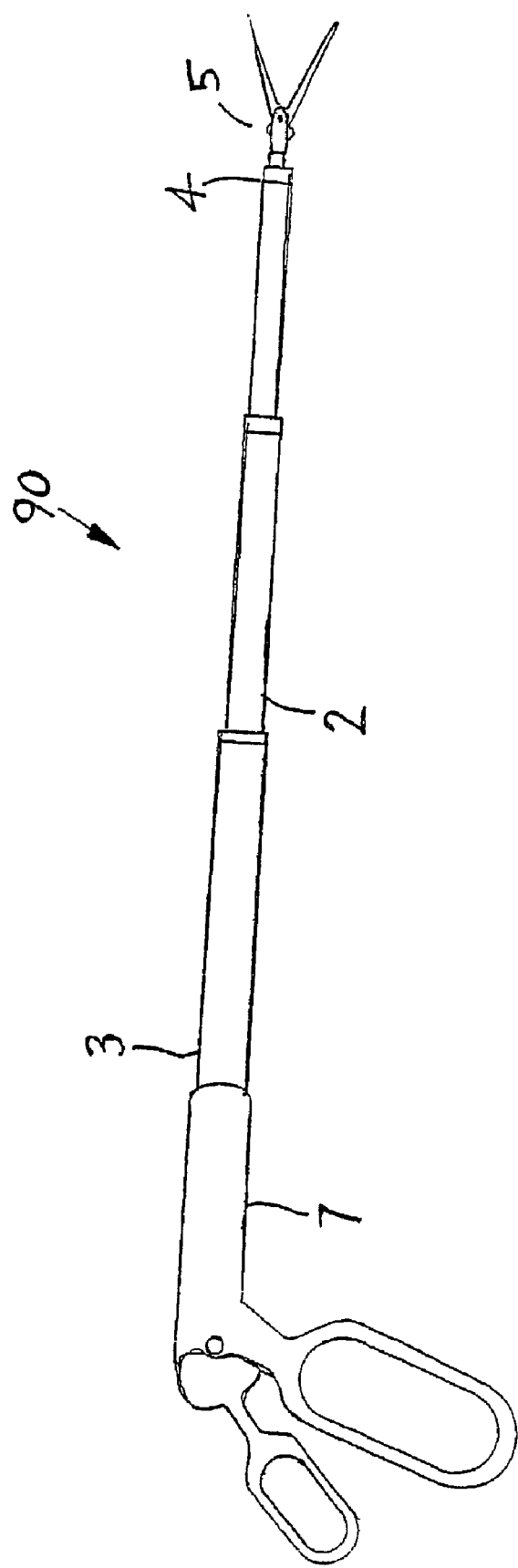
FIG. 42 is a side view of another minimally invasive surgical instrument according to the invention in a retracted configuration.
Figure 43:
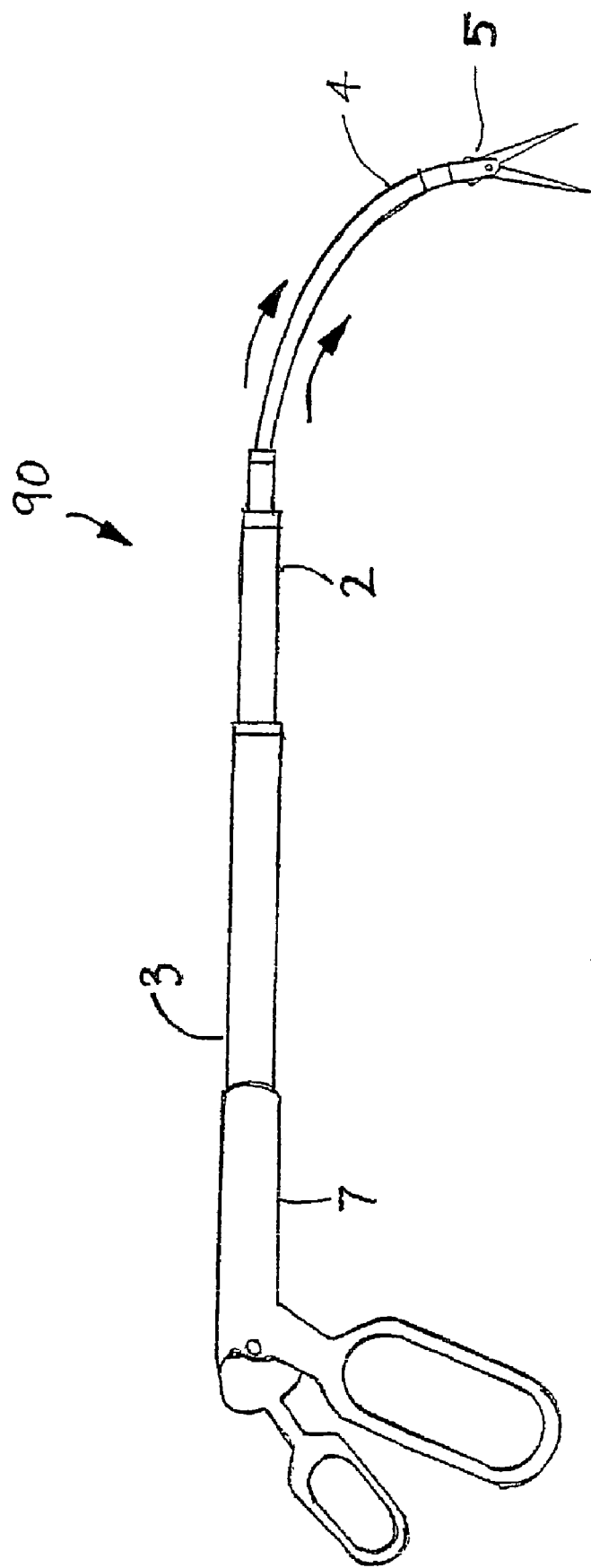
FIG. 43 is a side view of the instrument of FIG. 42 in an extended configuration.

FIGS. 42 and 43 illustrate another surgical instrument 90 according to the invention, which is similar to the surgical instrument 1 of FIGS. 1 to 29, and similar elements in FIGS. 42 and 43 are assigned the same reference numerals.

In this case, the stem 2 is extendable from a retracted configuration (FIG. 42) to an extended configuration (FIG. 43) in a telescopic manner.

It will be appreciated that the stem 2 may alternatively be extendable in a concertina manner, or in any other suitable manner.

The extendable stem 2 facilitates enhanced access for the end effector 5 at the distal end 4 of the stem 2 to desired locations in the operating space 12 for performing surgical procedures. The extendable aspect of the instrument 90 enables at least portion of the stem 2 to be rigid or flexible.

Figure 44:
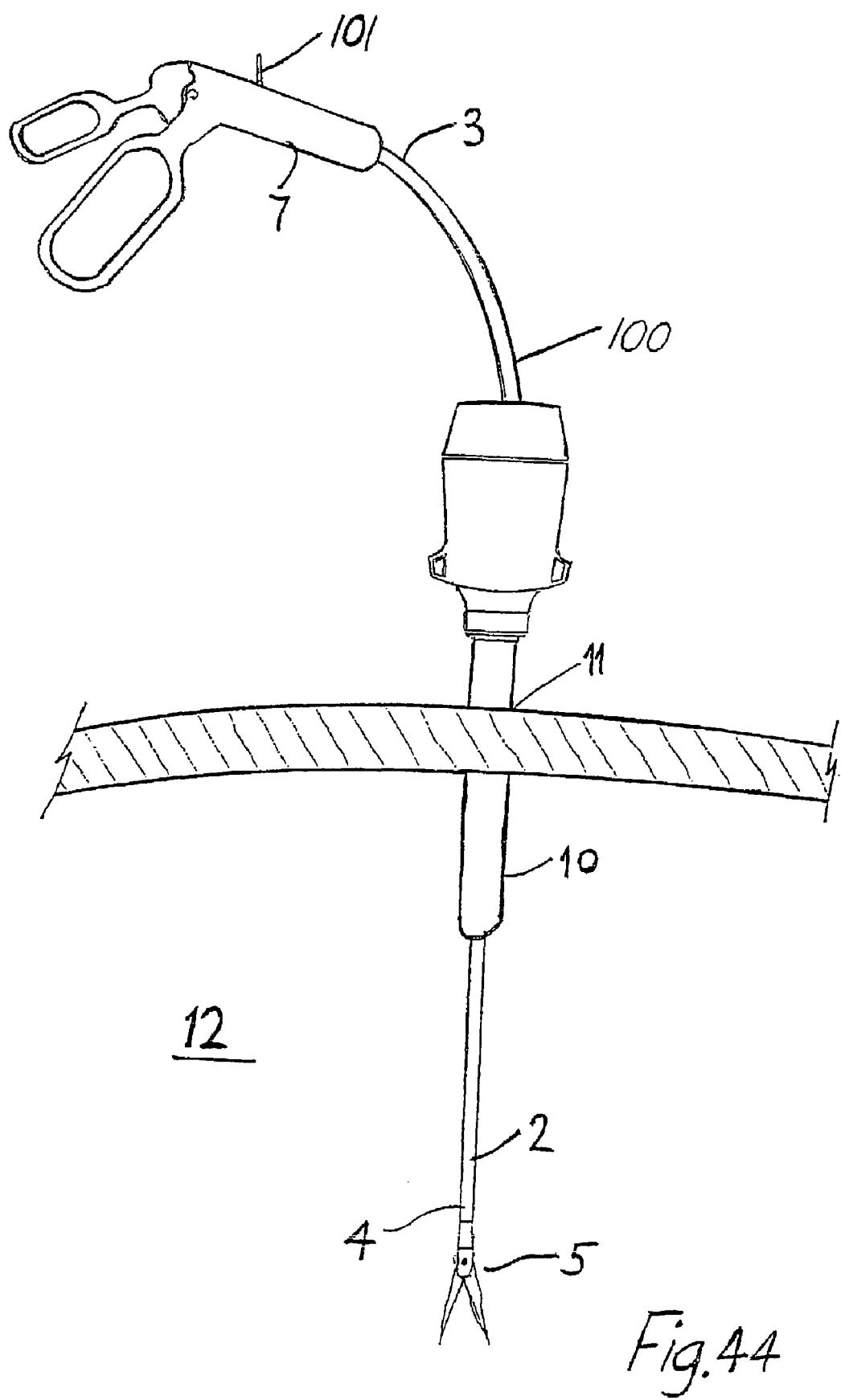
FIG. 44 is a schematic view of another minimally invasive surgical instrument according to the invention partially inserted through a cannula into an operating space.
Figure 45:
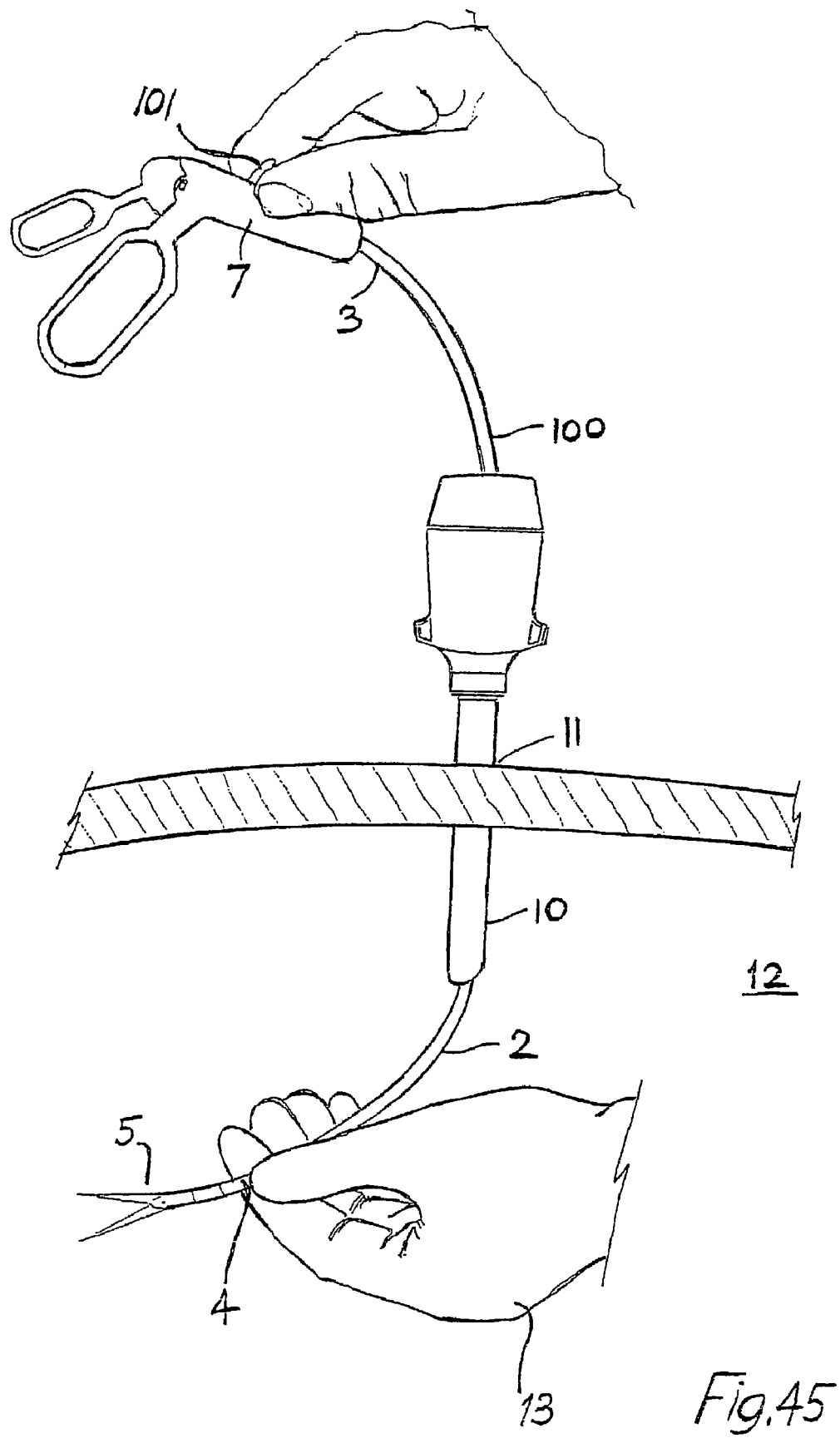
FIG. 45 is a schematic view illustrating manipulation of the instrument of FIG. 44 within the operating space, and locking of the instrument in the manipulated position and/or orientation.
Figure 46:
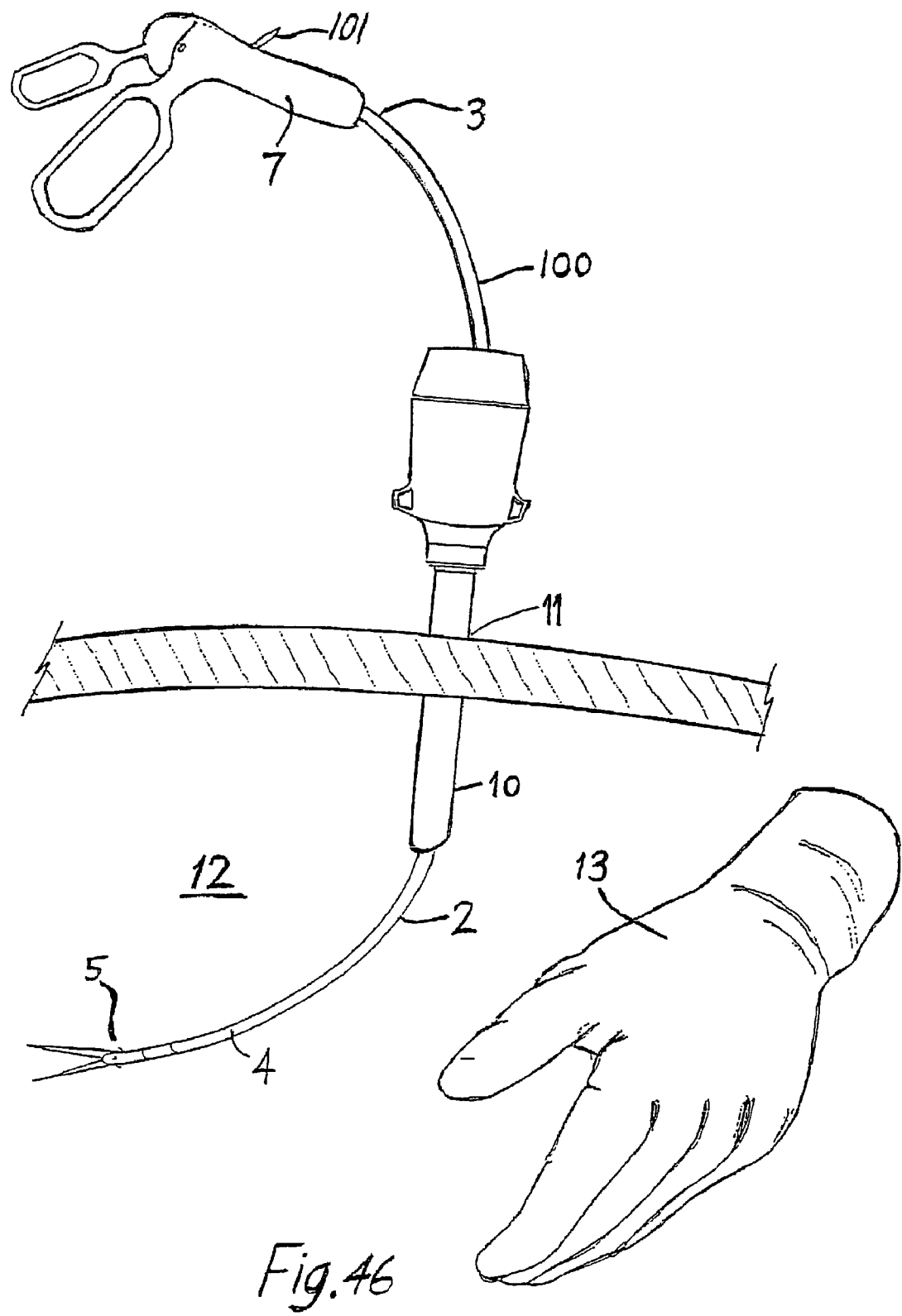
FIG. 46 is a schematic view of the instrument of FIG. 45 after manipulation and locking.

Referring to FIGS. 44 to 46, there is illustrated another surgical instrument 100 according to the invention, which is similar to the surgical instrument 1 of FIGS. 1 to 29, and similar elements in FIGS. 44 to 46 are assigned the same reference numerals.

In this case, the instrument 100 comprises means to lock the distal end 4 of the stem 2 in a desired manipulated position and/or orientation within the operating space 12.

The locking means ensures that the distal end 4 of the stem 2 maintains its desired manipulated position and/or orientation within the operating space 12, even if the stem 2 is inadvertently knocked against by the surgeon's hand 13, or by a laparoscopic instrument, or by an internal organ. The locking means also ensures that the malleable stem 2 maintains the desired position and/or orientation during insertion of the instrument 100 through the cannula 10. This is particularly advantageous if the cannula 10 is not completely flexible.

The means is provided, in this case, by at least one malleable wire 71, similar to wires 71 described previously with reference to FIG. 33, extending along at least portion of the stem 2. The wires 71 are slidably received in co-operating guides 72 on the stem 2, with stops at ends of the wires 71 to limit movement of the wires 71, and the wires 71 are connected proximally by a clamping arrangement to a locking switch 101 on the actuating handle 7 (FIG. 44).

In use, the instrument 100 is partially inserted through the cannula 10 into the operating space 12 so that the end effector 5 is located within the operating space 12. The distal end 4 of the stem 2 is manipulated into a desired position and/or orientation within the operating space 12 by the surgeon's hand 13, and the switch 101 is moved from the open position to the locked position to clamp the tensioned wires 71 in place (FIG. 45). With the switch 101 in the locked position, the distal end 4 of the stem 2 is locked in the manipulated position and/or orientation for increased security (FIG. 46).

It will be appreciated that the malleable wires 71 may alternatively be positioned along the interior of the stem 2, or embedded within the stem 2. It will further be appreciated that a coating, such as a low friction coating, may be provided over the wires 71.

An alternative construction for the malleable tube 22 of the outer shaft 20 of the stem 2 is illustrated in FIGS. 47 and 48. The tube 22, in this case, comprises an inner flexible tube 202 typically of a material such as polyvinylchloride (PVC), an intermediate tube 201, typically of a metal such as aluminium, and an outer malleable tube 200, typically of a material such as PVC. The PVC tubing 200, 202 helps to prevent kinking in the aluminium tube 201.

FIGS. 49 and 50 illustrate another alternative construction for the malleable tube 22. In this case, the tube 22 comprises a series of hinge joints 204 enclosed in an outer shrink-wrapped tube 203.

An alternative construction for the flexible cable 25 of the inner elongate member 23 of the stem 2 is illustrated in FIGS. 51 and 52. The cable 25, in this case, comprises a braid of inner wires 210.

FIGS. 53 and 54 illustrate another alternative construction for the flexible cable 25. In this case, the cable 25 comprises a series of chain linkages 211.

It will be appreciated that the instrument 1 is also suitable for use with a rigid cannula.

In one minimally invasive surgical instrument according to the invention, the end effector is mounted to the distal end of the stem before inserting the instrument partially through the laparoscopic cannula into an operating space. The end effector has a low-profile introduction configuration, and in this configuration the end effector is small enough, for example with a radial dimension in the range of from 2 mm to 15 mm, to be passed directly through the laparoscopic cannula.

In another minimally invasive surgical instrument according to the invention, the stem of the instrument is inserted partially through a laparoscopic cannula into an operating space, and the end effector is mounted to the distal end of the stem within the operating space. The stem of the instrument is small enough, for example with a radial dimension in the range of from 2 mm to 15 mm, to be passed directly through the laparoscopic cannula. The end effector may be inserted into the operating space by any suitable means, such as through a sealing access device, such as described in our International patent application published under number WO-A-00/32117.

The invention is not limited to the embodiments hereinbefore described, with reference to the accompanying drawings, which may be varied in construction and detail.

The invention claimed is:

1. A surgical instrument, comprising:
   a handle portion;
   a stem including a proximal portion coupled to the handle portion, and a distal portion having a bend; and
   an end effector coupled to a distal end of the bent stem by both a hinge joint and a rotational joint to allow pivoting and rotational movement of the end effector relative to the bent stem, the hinge joint and rotational joint being located proximal the end effector,
   wherein the rotational joint is distal of the hinge joint.

2. The surgical instrument of claim 1, wherein control of the hinge joint, rotational joint, and end effector, is provided at the handle portion.

3. The surgical instrument of claim 2, further comprising an actuator on the handle portion configured to control the hinge joint and the rotational joint.

4. The surgical instrument of claim 3, wherein the actuator includes a control dial configured to control the hinge joint and the rotational joint.

5. The surgical instrument of claim 3, wherein the actuator includes a switch member moveable between a first position for control of the rotational joint and a second position for control of the hinge joint.

6. The surgical instrument of claim 1, wherein the end effector includes a pair of grasping fingers or cutting fingers, and the handle portion affects movement of the grasping fingers or cutting fingers.

7. The surgical instrument of claim 1, wherein the proximal portion of the stem includes a straight portion.

8. The surgical instrument of claim 1, wherein the stem is configured to maintain a plurality of different desired bend orientations.

9. A surgical instrument, comprising:
a handle portion;
a stem including a proximal portion coupled to the handle portion, and a distal portion having a bend; and
an end effector coupled to a distal end of the bent stem,
the stem further comprising a hinge joint and a rotational joint being located proximal the end effector, and wherein the hinge joint is separate from the end effector, and
wherein the hinge joint is configured to allow pivoting movement of a portion of the stem distal portion containing the rotational joint.

10. The surgical instrument of claim 9, wherein control of the hinge joint, rotational joint, and end effector, is provided at the handle portion.

11. The surgical instrument of claim 10, further comprising an actuator on the handle portion configured to control the hinge joint and the rotational joint.

12. The surgical instrument of claim 11, wherein the actuator includes a control dial configured to control the hinge joint and the rotational joint.

13. The surgical instrument of claim 11, wherein the actuator comprises a switch member moveable between a first position for control of the rotational joint and a second position for control of the hinge joint.

14. The surgical instrument of claim 9, wherein the end effector includes a pair of grasping fingers or cutting fingers.

15. The surgical instrument of claim 9, wherein the proximal portion of the stem includes a straight portion.

16. A surgical instrument, comprising:
a handle portion;
a stem including a proximal portion coupled to the handle portion, and a distal portion having a bend;
an end effector coupled to a distal end of the bent stem;
a first hinge joint configured to allow pivoting movement of the stem distal portion proximal the end effector; and
a second joint separate from the first hinge joint and configured to allow pivoting movement of the end effector.

17. The surgical instrument of claim 16, further comprising a rotational joint configured to allow rotational movement of the end effector.

18. The surgical instrument of claim 16, further comprising an actuator on the handle portion configured to control the first hinge joint.

19. The surgical instrument of claim 16, wherein the end effector includes a pair of grasping fingers or cutting fingers.

20. The surgical instrument of claim 16, wherein the proximal portion of the stem includes a straight portion.

* * * * *

UNITED STATES PATENT AND TRADEMARK OFFICE
CERTIFICATE OF CORRECTION

| | | |
|---|---|---|
| PATENT NO. | : 8,157,817 B2 | Page 1 of 1 |
| APPLICATION NO. | : 10/347313 | |
| DATED | : April 17, 2012 | |
| INVENTOR(S) | : Frank Bonadio et al. | |

It is certified that error appears in the above-identified patent and that said Letters Patent is hereby corrected as shown below:

On the title page, item (75), lines 1-2,

"Alan Reid, Clontart (IE);" should read -- Alan Reid, Clontarf (IE); --

Signed and Sealed this
Third Day of July, 2012

David J. Kappos
*Director of the United States Patent and Trademark Office*